(12) United States Patent
Kaushikkar et al.

(10) Patent No.: US 7,992,098 B2
(45) Date of Patent: Aug. 2, 2011

(54) SYSTEM, METHOD, AND COMPUTER SOFTWARE PRODUCT FOR LINKED WINDOW INTERFACES

(75) Inventors: Shantanu V. Kaushikkar, San Jose, CA (US); Luis Jevons, Sunnyvale, CA (US)

(73) Assignee: Affymetrix, Inc., Santa Clara, CA (US)

( * ) Notice: Subject to any disclaimer, the term of this patent is extended or adjusted under 35 U.S.C. 154(b) by 1138 days.

(21) Appl. No.: 11/389,690

(22) Filed: Mar. 27, 2006

(65) Prior Publication Data

US 2006/0259874 A1 Nov. 16, 2006

Related U.S. Application Data

(63) Continuation of application No. 10/126,468, filed on Apr. 19, 2002, now abandoned, which is a continuation of application No. PCT/US01/26390, filed on Aug. 22, 2001.

(60) Provisional application No. 60/226,999, filed on Aug. 22, 2000, provisional application No. 60/286,578, filed on Apr. 26, 2001.

(51) Int. Cl.
*G06F 3/00* (2006.01)

(52) U.S. Cl. ........ 715/803; 715/700; 715/762; 715/763; 715/764; 715/765; 715/769; 715/771; 715/809; 715/810; 422/63

(58) Field of Classification Search ............... 422/63; 715/764, 700, 762, 763, 765, 769, 771, 809, 715/810
See application file for complete search history.

(56) References Cited

U.S. PATENT DOCUMENTS

| 4,016,557 | A | 4/1977 | Zitelli et al. |
| 4,218,733 | A | 8/1980 | Maselli |
| 4,410,799 | A | 10/1983 | Okamoto |
| 4,525,741 | A | 6/1985 | Chahal et al. |

(Continued)

FOREIGN PATENT DOCUMENTS

DE 3915692 11/1990

(Continued)

OTHER PUBLICATIONS

Axon Instruments, Inc. GenePix Pro 3.0 User's Guide, Mar. 8 2000.*

(Continued)

*Primary Examiner* — Ryan F Pitaro
(74) *Attorney, Agent, or Firm* — Thomas J. Siepmann

(57) ABSTRACT

Systems, methods, and computer program products are described for providing a graphical user interface (GUI) that may include a first openable window of image features constituting, for example, a pseudo-image of a scanned probe array. The image features each have one or more characteristics representing one or more hybridization reactions associated with a probe of the probe array. The GUI also has a second openable window including data features, each relating to one or more quantifications of one or more hybridization reactions associated with a probe of the probe array. This second window may be, for example, a scatter plot of hybridization intensities of probes to two or more labeled samples. The GUI further includes a third openable window including descriptive features such as rows of a spreadsheet. Each row may include descriptive elements associated with a probe. When a user selects a feature from any of the two or more windows, a corresponding feature in at least one other of the two or more windows is highlighted.

38 Claims, 9 Drawing Sheets

U.S. PATENT DOCUMENTS

| | | |
|---|---|---|
| 4,573,069 A | 2/1986 | Lewis, Jr. |
| 4,758,727 A | 7/1988 | Tomei et al. |
| 4,855,597 A | 8/1989 | Shimura |
| 4,877,966 A | 10/1989 | Tomei et al. |
| 5,030,924 A | 7/1991 | Fritz |
| 5,032,720 A | 7/1991 | White |
| 5,037,207 A | 8/1991 | Tomei et al. |
| 5,091,652 A | 2/1992 | Mathies et al. |
| 5,120,943 A | 6/1992 | Benz |
| 5,121,138 A | 6/1992 | Schermer et al. |
| 5,133,373 A | 7/1992 | Hoffman et al. |
| 5,143,854 A | 9/1992 | Pirrung et al. |
| 5,260,578 A | 11/1993 | Bliton et al. |
| 5,274,240 A | 12/1993 | Mathies et al. |
| 5,296,700 A | 3/1994 | Kumagai |
| 5,302,824 A | 4/1994 | Prager |
| 5,306,510 A | 4/1994 | Meltzer |
| 5,324,633 A | 6/1994 | Fodor et al. |
| 5,408,891 A | 4/1995 | Barber et al. |
| 5,411,065 A | 5/1995 | Meador et al. |
| 5,420,731 A | 5/1995 | Thomas et al. |
| 5,443,791 A | 8/1995 | Cathcart et al. |
| 5,445,934 A | 8/1995 | Fodor et al. |
| 5,474,744 A | 12/1995 | Lerch |
| 5,492,806 A | 2/1996 | Drmanac et al. |
| 5,525,464 A | 6/1996 | Drmanac et al. |
| 5,528,050 A | 6/1996 | Miller et al. |
| 5,532,874 A | 7/1996 | Stein |
| 5,538,613 A | 7/1996 | Brumley et al. |
| 5,540,891 A | 7/1996 | Portmann et al. |
| 5,551,487 A | 9/1996 | Gordon et al. |
| 5,578,832 A | 11/1996 | Trulson et al. |
| 5,585,639 A | 12/1996 | Dorsel et al. |
| 5,593,839 A | 1/1997 | Hubbell et al. |
| 5,603,342 A | 2/1997 | Shambaugh |
| 5,604,819 A | 2/1997 | Barnard |
| 5,607,861 A | 3/1997 | Komatsu et al. |
| 5,630,125 A | 5/1997 | Zellweger |
| 5,631,734 A | 5/1997 | Stern et al. |
| 5,689,110 A | 11/1997 | Dietz et al. |
| 5,700,637 A | 12/1997 | Southern |
| 5,706,364 A | 1/1998 | Kopec et al. |
| 5,714,756 A | 2/1998 | Park et al. |
| 5,721,435 A | 2/1998 | Troll |
| 5,756,050 A | 5/1998 | Ershow et al. |
| 5,760,951 A | 6/1998 | Dixon et al. |
| 5,763,870 A | 6/1998 | Sadler et al. |
| 5,770,151 A | 6/1998 | Roach et al. |
| 5,798,035 A | 8/1998 | Kirk et al. |
| 5,800,992 A | 9/1998 | Fodor et al. |
| 5,807,522 A | 9/1998 | Brown et al. |
| 5,834,758 A | 11/1998 | Trulson et al. |
| 5,856,101 A | 1/1999 | Hubbell et al. |
| 5,874,219 A | 2/1999 | Rava et al. |
| 5,882,930 A | 3/1999 | Baier |
| 5,895,915 A | 4/1999 | DeWeerd et al. |
| 5,897,837 A | 4/1999 | Mizuno |
| 5,900,613 A | 5/1999 | Koziol et al. |
| 5,916,747 A | 6/1999 | Gilchrist et al. |
| 5,922,617 A | 7/1999 | Wang et al. |
| 5,925,525 A | 7/1999 | Fodor et al. |
| 5,936,324 A | 8/1999 | Montagu |
| 5,939,719 A | 8/1999 | Park et al. |
| 5,981,956 A | 11/1999 | Stern |
| 5,984,474 A | 11/1999 | Schweitzer et al. |
| 5,998,141 A | 12/1999 | Acton |
| 6,004,991 A | 12/1999 | Fourtillan et al. |
| 6,025,601 A | 2/2000 | Trulson et al. |
| 6,040,193 A | 3/2000 | Winkler et al. |
| 6,069,984 A | 5/2000 | Sadler et al. |
| 6,072,624 A | 6/2000 | Dixon et al. |
| 6,075,613 A | 6/2000 | Schermer et al. |
| 6,078,390 A | 6/2000 | Bengtsson |
| 6,083,763 A | 7/2000 | Balch |
| 6,090,251 A | 7/2000 | Sundberg et al. |
| 6,090,555 A | 7/2000 | Fiekowsky et al. |
| 6,097,025 A | 8/2000 | Modlin et al. |
| 6,101,946 A | 8/2000 | Martinsky et al. |
| 6,110,426 A | 8/2000 | Shalon et al. |
| 6,130,440 A | 10/2000 | Ogura |
| 6,141,096 A | 10/2000 | Stern et al. |
| 6,151,123 A | 11/2000 | Nielsen |
| 6,157,700 A | 12/2000 | Sako |
| 6,166,385 A | 12/2000 | Webb et al. |
| 6,169,289 B1 | 1/2001 | White et al. |
| 6,171,793 B1 | 1/2001 | Phillips et al. |
| 6,180,351 B1 | 1/2001 | Cattell |
| 6,185,030 B1 | 2/2001 | Overbeck |
| 6,188,783 B1 | 2/2001 | Balaban et al. |
| 6,201,639 B1 | 3/2001 | Overbeck |
| 6,207,960 B1 | 3/2001 | Stern |
| 6,209,983 B1 | 4/2001 | Osborne et al. |
| 6,211,913 B1 | 4/2001 | Hansen et al. |
| 6,211,989 B1 | 4/2001 | Wulf et al. |
| 6,215,894 B1 | 4/2001 | Zeleny et al. |
| 6,218,803 B1 | 4/2001 | Montagu et al. |
| 6,222,664 B1 | 4/2001 | Dorsel et al. |
| 6,225,625 B1 | 5/2001 | Pirrung et al. |
| 6,229,607 B1 | 5/2001 | Shirai et al. |
| 6,236,456 B1 | 5/2001 | Giebeler et al. |
| 6,245,507 B1 | 6/2001 | Bogdanov |
| 6,284,465 B1 | 9/2001 | Wolber |
| 6,287,880 B1 | 9/2001 | Erickson et al. |
| 6,301,550 B1 | 10/2001 | Okamoto et al. |
| 6,309,601 B1 | 10/2001 | Juncosa et al. |
| 6,309,822 B1 | 10/2001 | Fodor et al. |
| 6,312,914 B1 | 11/2001 | Kardos et al. |
| 6,320,196 B1 | 11/2001 | Dorsel et al. |
| 6,323,852 B1 | 11/2001 | Blower, Jr. et al. |
| 6,342,927 B1 | 1/2002 | Kimoto et al. |
| 6,345,115 B1 | 2/2002 | Ramm et al. |
| 6,349,144 B1 | 2/2002 | Shams |
| 6,353,475 B1 | 3/2002 | Jensen et al. |
| 6,355,934 B1 | 3/2002 | Osgood et al. |
| 6,362,004 B1 | 3/2002 | Noblett |
| 6,371,370 B2 | 4/2002 | Sadler et al. |
| 6,406,849 B1 | 6/2002 | Dorsel et al. |
| 6,407,858 B1 | 6/2002 | Montagu |
| 6,447,723 B1 | 9/2002 | Schermer et al. |
| 6,453,241 B1 * | 9/2002 | Bassett et al. .................. 702/19 |
| 6,466,309 B1 | 10/2002 | Kossakovski et al. |
| 6,469,513 B1 | 10/2002 | Tse |
| 6,471,916 B1 | 10/2002 | Noblett |
| 6,490,533 B2 | 12/2002 | Weiner et al. |
| 6,519,583 B1 * | 2/2003 | Koleszar et al. ..................... 1/1 |
| 6,562,565 B1 | 5/2003 | Pinkel et al. |
| 6,567,163 B1 | 5/2003 | Sandstrom |
| 6,587,579 B1 | 7/2003 | Bass |
| 6,591,196 B1 | 7/2003 | Yakhini et al. |
| 6,650,364 B1 | 11/2003 | Itani et al. |
| 6,679,844 B2 | 1/2004 | Loftman et al. |
| 6,741,124 B2 | 5/2004 | Lucas |
| 6,750,906 B1 | 6/2004 | Itani et al. |
| 6,768,820 B1 | 7/2004 | Yakhini et al. |
| 6,913,200 B2 | 7/2005 | Sillman et al. |
| 7,062,092 B2 | 6/2006 | Kaushikkar et al. |
| 2002/0024026 A1 | 2/2002 | Kaushikkar et al. |
| 2002/0025082 A1 | 2/2002 | Kaushikkar et al. |
| 2002/0047853 A1 | 4/2002 | Bartell |
| 2002/0074512 A1 | 6/2002 | Montagu et al. |
| 2002/0088858 A1 | 7/2002 | Tanaami et al. |
| 2002/0147512 A1 | 10/2002 | Bernhart et al. |
| 2002/0150935 A1 | 10/2002 | Zhou et al. |
| 2002/0159057 A1 | 10/2002 | Odoy et al. |
| 2002/0160369 A1 | 10/2002 | Dorsel et al. |
| 2002/0168094 A1 | 11/2002 | Kaushikkar et al. |
| 2003/0059094 A1 | 3/2003 | Cattell et al. |
| 2003/0073896 A1 | 4/2003 | Zuzan et al. |
| 2003/0124589 A1 | 7/2003 | Piper |
| 2003/0203492 A1 | 10/2003 | Sillman |
| 2004/0006431 A1 | 1/2004 | Bartell et al. |
| 2004/0033485 A1 | 2/2004 | Li et al. |
| 2004/0064264 A1 | 4/2004 | Corson et al. |
| 2004/0094626 A1 | 5/2004 | Sillman et al. |
| 2005/0031178 A1 | 2/2005 | Park |

FOREIGN PATENT DOCUMENTS

| | | |
|---|---|---|
| EP | 0935210 | 8/1999 |
| EP | 1043667 | 10/2000 |
| EP | 1186673 | 3/2002 |
| EP | 1429137 | 6/2004 |
| EP | 1480284 | 11/2004 |
| WO | WO 98/07022 | 2/1998 |
| WO | WO 98/35223 | 8/1998 |
| WO | WO 00/39338 | 6/2000 |
| WO | WO 00/39338 | 7/2000 |

OTHER PUBLICATIONS

Bio Discovery, Inc. Imagene Tutorial, Sep. 20, 1999.*

BioDiscovery, Inc., ImaGene Version 3.0 User's Manual, Sep. 20, 1999, pp. 1-66, BioDiscovery, Inc., Marina del Rey, CA, United States.

Kalocsai P. et al., Visualization and Analysis of Gene Expression Data, Journal of the Association for Laboratory Automation, 1999, pp. 58-61, vol. 4, No. 5.

Axon Instruments, Inc.; Press release dated Mar. 8, 2000 entitled, "Axon Instruments Announces Release of GenePix Pro 3.0"; http://www.axon.com/press/pr20000308.htm.

Bowtell; Options available—from start to finish—for obtaining expression data by microarray; Nature Genetics, New York, NY, US; vol. 21; No. Suppl; Jan. 1999; pp. 25-32.

Communication from European Patent Office dated Apr. 7, 2004, enclosing the European Search Report for EP Application No. 0324896, and Annex to the EP Search Report.

Communication from European Patent Office dated Sep. 6, 2004, enclosing the European Search Report for EP Application No. 0324895, and Annex to the EP Search Report.

Cortese; Array of Options: Instrumentation to exploint the DNA microarray explosion; Scientist Institute for Scientific Information; vol. 14, No. 11; May 29, 2000; pp. 1-4.

Eick S. G.; Visualizing Multi-dimensional data; Computer graphics; vol. 34, No. 1; Feb. 2000; pp. 61-67.

GenePix Pro 3.0 Software, http://www.apbiotech.com/application/microarray/GenePix_Pro3.htm. GenePix Pro Features, pp. 1-19. Jul. 20, 2001.

International Search Report Issued in PCT application PCT/US01/26390. May 31, 2002.

Jean Montagu and Nathan Weiner; Fluorescence Array Scanner Employing a Flying Objective; Journal of the Association for Laboratory Automation; Mar. 1999; vol. 4; No. 1; pp. 40-43.

Khan et al; DNA microarray technology the anticipated impact on the study of human disease; Biochimica et Biophysica Acta, Amsterdam, NL; vol. 1423, No. 2; Mar. 25, 1999; pp. M17-M28.

Meyer et al; Visualization of data; Current opinion in Biotechnology; vol. 11, No. 1; Feb. 2000; pp. 89-96.

Xiang et al: cDNA microarray technology and its applications; Biotechnology Advances; Elsevier Publishing, Barking, GB; vol. 18; No. 1; Mar. 2000; pp. 35-46.

* cited by examiner

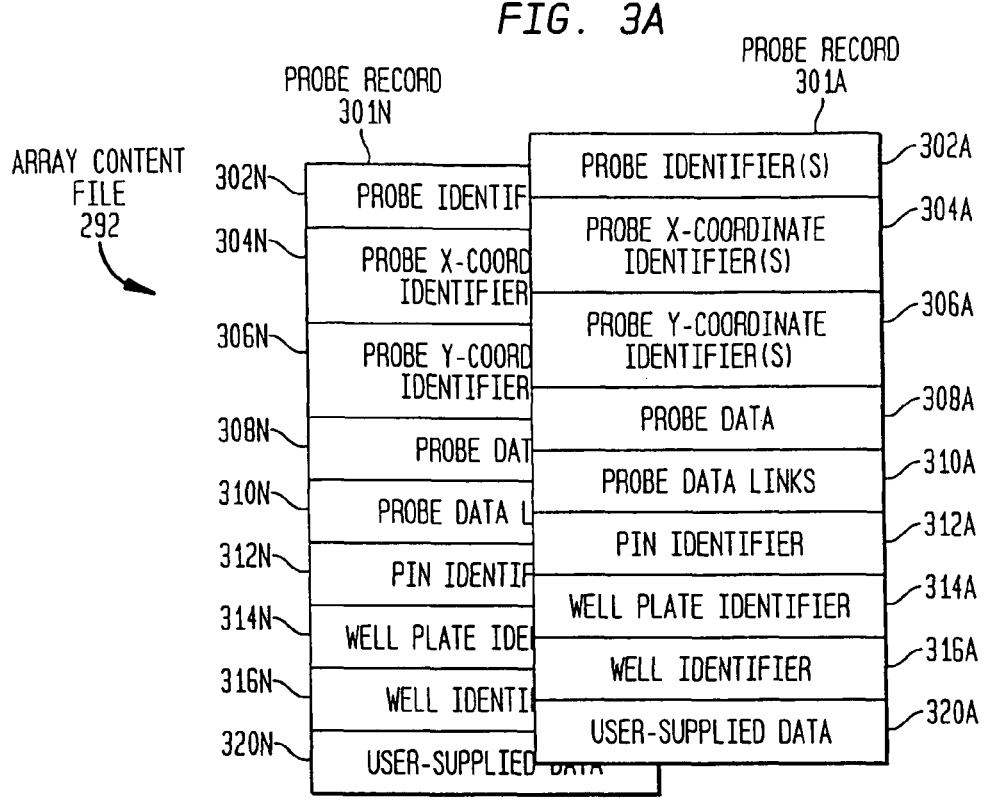
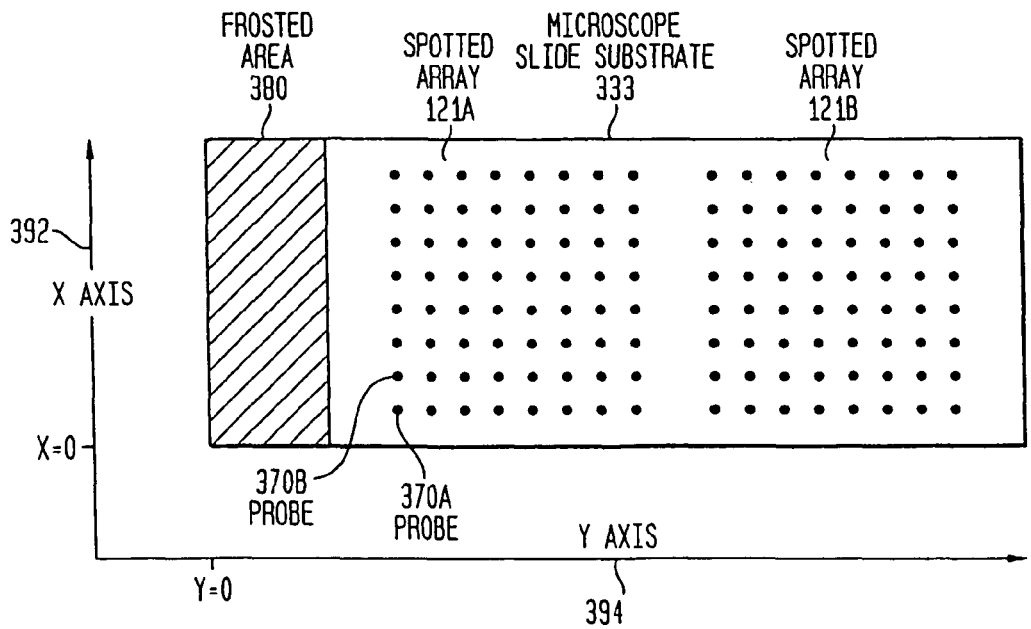

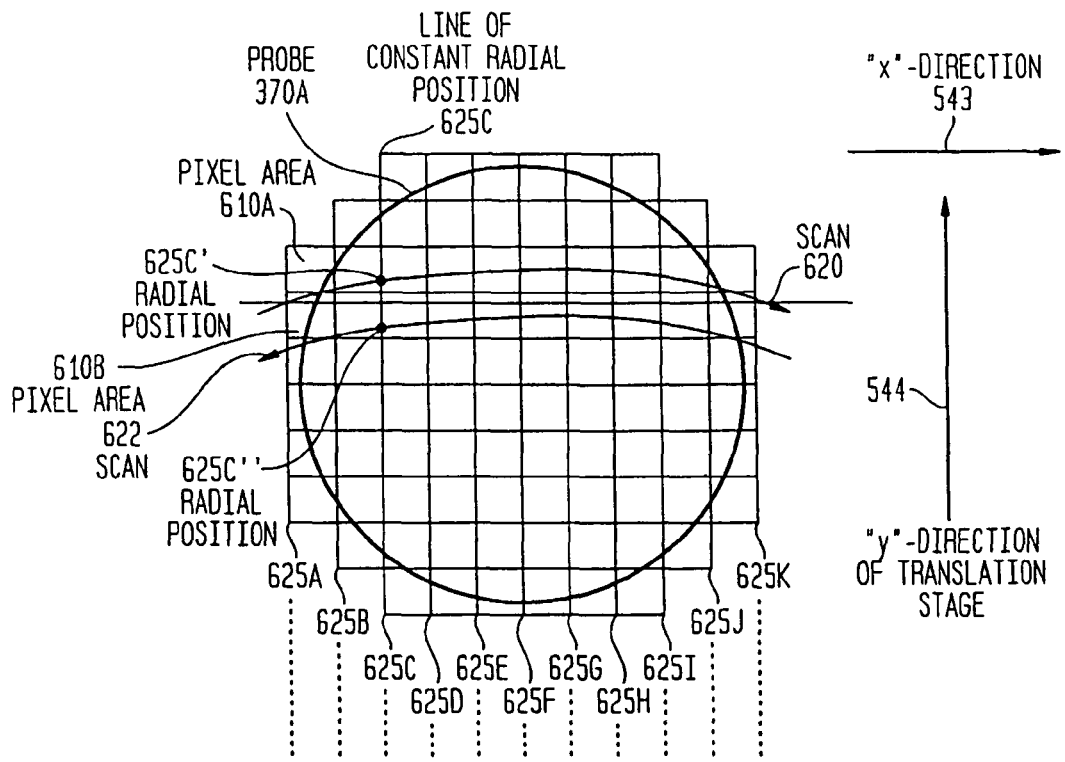
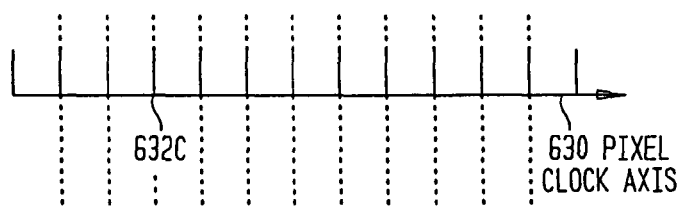
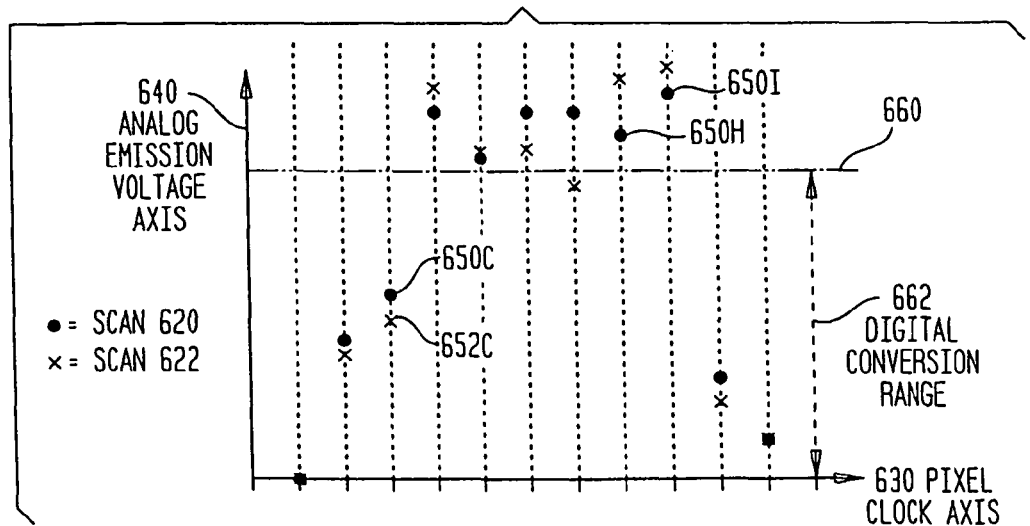

SYSTEM, METHOD, AND COMPUTER SOFTWARE PRODUCT FOR LINKED WINDOW INTERFACES

RELATED APPLICATIONS

This application is a continuation of U.S. application Ser. No.: 10/126,468, filed on Apr. 19, 2002 now abandoned, which is a continuation of PCT Application PCT/US01/26390 filed on Aug. 22, 2001, which claims priority from U.S. Provisional Application 60/226,999, entitled "System, Method, and Product for Linked Window Interface," filed on Aug. 22, 2000; and U.S. Provisional Application No. 60/286,578, System, Method, and Product for Scanning of Biological Materials," filed Apr. 26, 2001. all of which are hereby incorporated herein by reference in their entireties for all purposes.

BACKGROUND OF THE INVENTION

1. Field of the Invention

The present invention relates to computer systems, methods, and products for analyzing and displaying scanned images of high-density arrays of biological materials.

2. Related Art

Synthesized probe arrays, such as Affymetrix® GeneChip® arrays, have been used to generate unprecedented amounts of information about biological systems. For example, a commercially available GeneChip® array set from Affymetrix, Inc. of Santa Clara, Calif., is capable of monitoring the expression levels of approximately 6,500 murine genes and expressed sequence tags (EST's). Experimenters can quickly design follow-on experiments with respect to genes, EST's, or other biological materials of interest by, for example, producing in their own laboratories microscope slides containing dense arrays of probes using the Affymetrix® 417™ Arrayer or other spotting devices.

Analysis of data from experiments with synthesized and/or spotted probe arrays may lead to the development of new drugs and new diagnostic tools. In some conventional applications, this analysis begins with the capture of fluorescent signals indicating hybridization of labeled target samples with probes on synthesized or spotted probe arrays. The devices used to capture these signals often are referred to as scanners, an example of which is the Affymetrix® 428™ Scanner from Affymetrix.

There is a great demand in the art for methods for organizing, accessing, analyzing, and displaying the vast amount of information collected by scanning microarrays. Computer-based systems and methods have been developed to assist a user to obtain and visualize the vast amounts of information generated by the scanners. These commercial and academic software applications typically provide such information as intensities of hybridization reactions or comparisons of hybridization reactions. This information may be displayed to a user in graphical form.

SUMMARY OF THE INVENTION

The present invention includes a system, a method, and a computer program product for controlling an optical scanner. Systems, methods, and computer program products are described with respect to some embodiments for providing a graphical user interface (GUI). The GUI may include a first openable window of image features constituting, for example, a pseudo-image of a scanned probe array. The term "pseudo-image" is used in this context to mean that the image features provide a graphical representation of the probes of a probe array that typically are based on emissions from probe-target pairs, lack of emissions from probes that have not hybridized with targets, and information about the location of the probes on the probe array. The word "openable" is used in this context to mean that the window may be opened, e.g. by a user, so as to be displayed in the GUI, but may also be closed or otherwise not displayed. The image features have one or more characteristics representing one or more hybridization reactions associated with a probe of the probe array.

The GUI of these embodiments also has a second openable window including data features, each relating to one or more quantifications of one or more hybridization reactions associated with a probe of the probe array. This second window may be, for example, a scatter plot of hybridization intensities of probes to two or more labeled samples. The GUI further includes a third openable window including descriptive features such as rows of a spreadsheet. Each row may include descriptive elements associated with a probe. In some implementations, when a user selects a feature from any of the two or more windows, a corresponding feature in at least one other of the two or more windows is highlighted. For example, a user may select an image feature in the first window (e.g., a spot representing a probe of a spotted array), thereby causing a spot in the scatter plot and a row in the spreadsheet to be highlighted. The spot in the scatter plot and the spreadsheet row provide information about the probe corresponding to the image feature selected by the user in the first window.

The probes may be those of a spotted probe array such as may be generated, for example, by an Affymetrix® 417™ or 427™ Arrayer. As another non-limiting example, the probes may be those synthesized on a synthesized array such as an Affymetrix® GeneChip® array.

With respect to the first window, the graphically represented probes have one or more characteristics indicative of the efficiency or intensity of hybridization associated with the corresponding probe. For example, the intensity or another visual characteristic of the image features graphically representing probes may be varied to indicate the efficiency or intensity of hybridization. With respect to the example of the second window constituting a scatter plot, the plot may show along one axis the intensity of emissions from a first label such as a dye that fluoresces in response a first excitation source. The scatter plot may show along another axis the intensity of emissions from a second dye that fluoresces in response the same or another excitation source. The scatter plot need not be limited to two dimensions, as when, for example, a third dye is associated with probe-target pairs hybridized on the probe array. Any form of labeling may be used, and many types of graphs may be employed that provide, for example, visual comparisons between two or more sets of hybridization data.

A third of the two or more windows may include a table, spreadsheet, or other textual or graphical representation of information related to probes in the probe array. In some implementations, for example, a third window may include a spreadsheet having rows (or, in other aspects, columns, or combinations thereof) containing any of a variety of data. For example, the data may relate to the experiment that produced the hybridization intensities represented by a pseudo-image in the first window, e.g., the type of dye or dyes used in the experiment. The data may also include links to sources, such as on the Internet or another database source, containing information about the probes and/or the targets that hybridized with the probes. As yet another non-limiting example, the data may include statistical information about the absolute or relative intensities of the probes. As a further non-limiting example, the data may include notes, labels, or other information provided by the user.

In some implementations, two or more of the windows are simultaneously displayed to the user on a display device. The user may select a graphical element of one of the simultaneously displayed windows and a corresponding graphical element on another of the two or more windows is highlighted. The highlighting may be done in accordance with any of a variety of known techniques, such as by changing the font and/or color of foreground or background, or by providing special effects such as blinking.

A fourth window may also be opened in some implementations. This fourth window may, like the first window, include image features having one or more characteristics representing one or more hybridization reactions associated with a probe of the probe array. For example, the image features of the first window may have characteristics (such as color or gray-scale intensity) representing the degree, efficiency, or intensity of hybridization of a first sample labeled with a first fluorescent dye to the probes of a spotted array. The image features of the second window may have characteristics representing the degree, efficiency, or intensity of hybridization of a second sample labeled with a second fluorescent dye to the probes of the same spotted array. As another example, the image features of the first window may represent the degree, efficiency, or intensity of hybridization of a first sample labeled with a first fluorescent dye to the probes of a first synthesized array, and the mage features of the second window may represent the degree, efficiency, or intensity of hybridization of a second sample labeled with a the same or another fluorescent dye to the probes of a second synthesized array having probes essentially the same as the probes of the first synthesized array.

The characteristics of the image features of the first and/or fourth window may include a chromatic value representing degree, efficiency, or intensity of hybridization. For example, the chromatic value may be a hue (color), brightness, lightness, or saturation value. The characteristic may also, or in addition, be an intensity value. The intensity value may be, for example, a gray-scale value.

The second openable window may, in some embodiments, include a histogram wherein the plurality of data features comprises bars, each representing a quantification of a number of probes having in common a range of degree, efficiency, or intensity of hybridization with one or more targets. The second openable window may also be any other kind of representation of statistical information about absolute or relative hybridization of probes such as may be conveyed, for example, by a scatter plot (as noted), a bar graph, or a line graph.

With respect to the third openable window, the descriptive features may, as one example, constitute rows of a spreadsheet. Each row may include one or more descriptive elements associated with a probe. Non-limiting examples of descriptive elements include any one or combination of two or more of the following: absolute image intensity value, relative image intensity value, user-supplied data related to the probe, biological information related to the probe; probe identifier, probe x-coordinate identifier, probe y-coordinate identifier, probe-related data, probe data links, pin identifier, and/or well plate identifier. The probe data links may include links to remotely or locally stored user-supplied data related to the probe, and/or links to remotely or locally stored biological information related to the probe. The probe-related data may include chromosome location of a gene or EST represented by the probe, band location on the chromosome, and/or SNP or other marker identifying the location on the chromosome.

In accordance with other embodiments, a user interface is described that includes any combination of two or more of the following windows: a first window having a plurality of image features, each having one or more characteristics representing one or more hybridization reactions associated with a probe of a probe array; a second window having a plurality of data features, each relating to one or more quantifications of one or more hybridization reactions associated with a probe of the probe array; and a third window having a plurality of descriptive features, each including one or more descriptive elements associated with a probe of the probe array. In these embodiments, when a user selects a feature from any of the two or more windows, a corresponding feature in at least one other of the two or more windows is highlighted.

In accordance with yet other embodiments, a computer program product is described. This product includes an image processor that processes image data based on scanning a probe array, and a GUI manager constructed and arranged to provide two or more windows. The windows may be any combination of the following: (i) a first window having a plurality of image features based on the processed image data, each having one or more characteristics representing one or more hybridization reactions associated with a probe of the probe array, (ii) a second window having a plurality of data features, each relating to one or more quantifications of one or more hybridization reactions associated with a probe of the probe array, and/or (iii) a third window having a plurality of descriptive features, each including one or more descriptive elements associated with a probe of the probe array. When a user selects a feature from any of the two or more windows, the GUI manager may, in some implementations, cause a corresponding feature in at least one other of the two or more windows to be highlighted.

Also described is a computer program product having a GUI manager that provides two or more windows. These windows may be any combination of (i) a first window having a plurality of image features, each having one or more characteristics representing one or more hybridization reactions associated with a probe of the probe array, (ii) a second window having a plurality of data features, each relating to one or more quantifications of one or more hybridization reactions associated with a probe of the probe array, and (iii) a third window having a plurality of descriptive features, each including one or more descriptive elements associated with a probe of the probe array.

In accordance with yet other embodiments, a method is described that includes providing image data based on scanning a probe array and providing, in a graphical user interface, two or more windows. These windows are selected from the group consisting of (i) a first window having a plurality of image features based on the image data, each having one or more characteristics representing one or more hybridization reactions associated with a probe of a probe array, (ii) a second window having a plurality of data features, each relating to one or more quantifications of one or more hybridization reactions associated with a probe of the probe array, and (iii) a third window having a plurality of descriptive features, each including one or more descriptive elements associated with a probe of the probe array.

Also included in the following description is a scanning system that includes a scanner that scans a probe array to generate image data, an image processor that processes the image data, and a GUI manager that provides two or more windows. These windows may be any combination of the following: (i) a first window having a plurality of image features based on the processed image data, each having one or more characteristics representing one or more hybridization reactions associated with a probe of the probe array, (ii) a second window having a plurality of data features, each relating to one or more quantifications of one or more hybridization reactions associated with a probe of the probe array, and (iii) a third window having a plurality of descriptive features, each including one or more descriptive elements associated with a probe of the probe array.

Yet another described embodiment is a scanning system. This system includes a scanner that scans a probe array to generate image data, a computer, and a computer program product. When executed on the computer, the computer program product performs a method comprising the steps of processing the image data and providing, in a graphical user interface, two or more windows. These windows may be any combination of the following: (i) a first window having a plurality of image features based on the processed image data, each having one or more characteristics representing one or more hybridization reactions associated with a probe of a probe array, (ii) a second window having a plurality of data features, each relating to one or more quantifications of one or more hybridization reactions associated with a probe of the probe array, and (iii) a third window having a plurality of descriptive features, each including one or more descriptive elements associated with a probe of the probe array.

Generally, one advantage provided by the preceding and other embodiments is that data regarding probe-target hybridization, and the probes associated with the hybridization reactions, may be simultaneously displayed to a user in a variety of forms. These forms may include, for example, two or more of a pseudo-image of probe-target hybridization (and probes that did not hybridize with targets); a statistical representation of absolute or relative hybridization (such as in a scatter plot); and/or a table of processed, derived, calculated, retrieved, and/or user-supplied information related to the probes. By selecting a feature corresponding to a probe or probes in one of these windows, other information related to the same probe or probes may be highlighted in the same or other window or windows for the benefit of the user.

According to yet another embodiment, a computer system for providing a user interface with a scanner for scanning a probe array to generate image data includes two or more window means. These window means may include a first window means for providing image feature means having one or more characteristics representing one or more hybridization reactions associated with probe means of a probe array; and a second window means for providing a data feature means related to one or more quantification means of said one or more hybridization reactions associated with probe means of the probe array. These window means may also include a third window means for providing descriptive feature means including one or more descriptive elements associated with probe means of the probe array.

According to yet another embodiment, a computer system for providing a user interface with a scanner for scanning a probe array is programmed to display image features having one or more characteristics representing one or more hybridization reactions associated with a probe of the probe array, data features related to one or more quantifications of one or more hybridization reactions associated with a probe of the probe array, and descriptive features including one or more descriptive elements associated with a probe of the probe array.

According to yet another embodiment, a computer program product includes a GUI manager. The GUI manager is constructed and arranged to provide display regions for displaying image features representing hybridization associated with a probe of a probe array, data features related to quantifying the hybridization associated with a probe of the probe array, and descriptive features associated with a probe of the probe array.

According to yet another embodiment, a computer program includes a GUI manager for providing window means for displaying image feature means representing hybridization means associated with a probe means of a probe array, for displaying data feature means related to quantifying hybridization means associated with probe means of the probe array, and for displaying descriptive feature means associated with probe means of the probe array.

The above embodiments, implementations, and aspects are not necessarily inclusive or exclusive of each other and may be combined in any manner that is non-conflicting and otherwise possible, whether they be presented in association with a same, or a different, aspect of the invention. The description of one embodiment, implementation, or aspect is not intended to be limiting with respect to other embodiments or implementations. Also, any one or more function, step, operation, or technique described elsewhere in this specification may, in alternative embodiments or implementations, be combined with any one or more function, step, operation, or technique described in the summary. Thus, the above embodiments, implementations, and aspects are illustrative rather than limiting.

BRIEF DESCRIPTION OF THE DRAWINGS

FIG. 3A is a graphical representation of data records in one embodiment of a data file suitable for storing data regarding spotted arrays produced in cooperation with the user computer of FIG. 2 and the arrayer of FIG. 1.

FIG. 3B is a graphical representation of a microscope slide including illustrative embodiments of spotted arrays produced in cooperation with the user computer of FIG. 2 and the arrayer of FIG. 1.

FIG. 6A is a graphical representation of one embodiment of a probe feature showing bidirectional scanning lines such as may be implemented using the scanning arm of FIGS. 5A and 5B.

FIG. 6B is an illustrative plot of pixel clock pulses aligned with the scanned probe feature of FIG. 6A to show illustrative radial position sampling points.

FIG. 6C is an illustrative plot of sampled analog emission voltages aligned with the pixel clock pulses of FIG. 6B.

Figure 1:
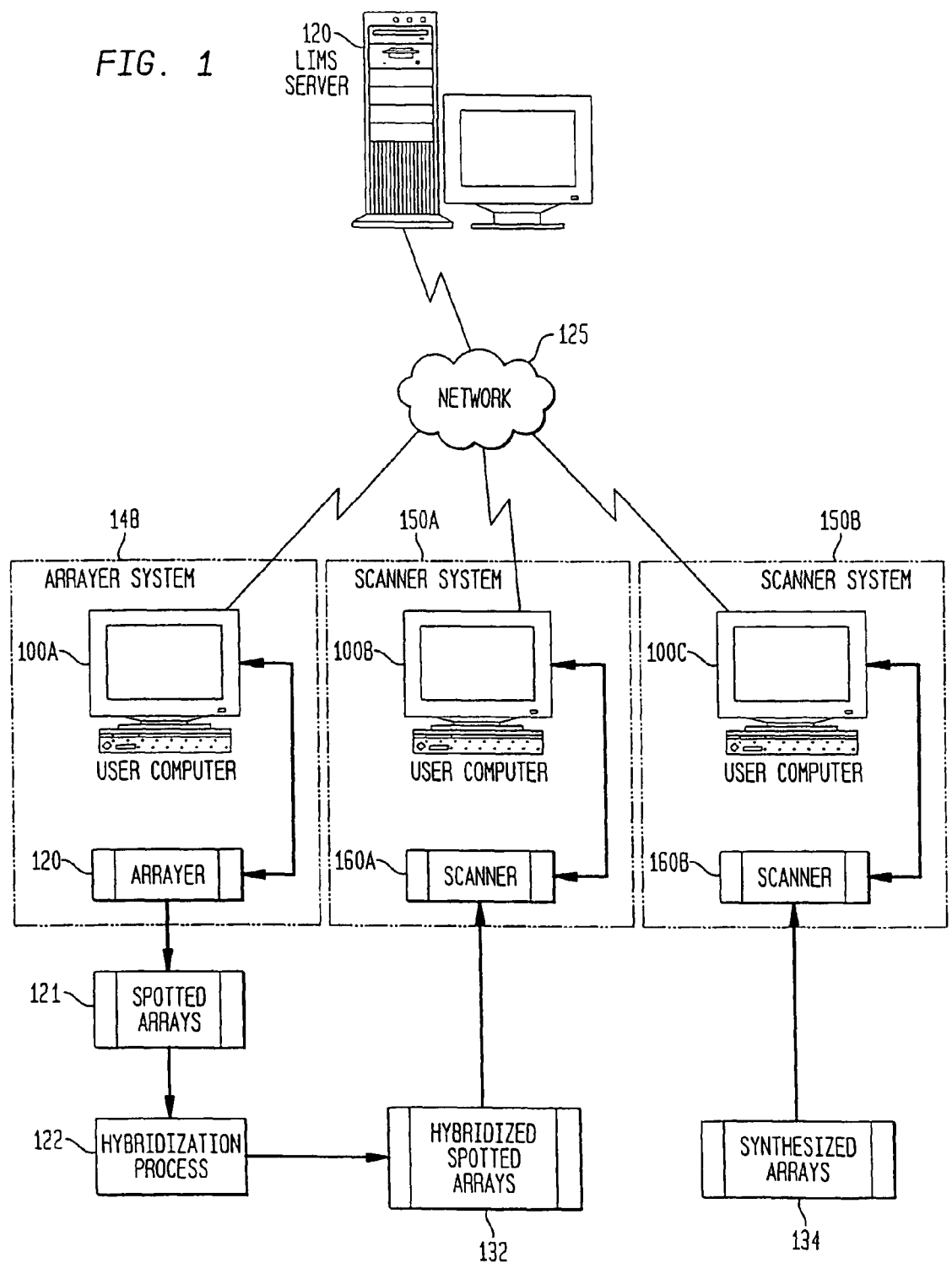
FIG. 1 is a simplified schematic diagram of one embodiment of networked systems for generating, sharing, and processing probe array data among computers on a network, including an arrayer system for generating spotted probe arrays and scanner systems for scanning spotted and synthesized probe arrays.

The described features will be more clearly appreciated from the following detailed description when taken in conjunction with the accompanying drawings. In the drawings, like reference numerals indicate like structures or method steps and the leftmost digit of a reference numeral indicates the number of the figure in which the referenced element first. In functional block diagrams, rectangles generally indicate functional elements, parallelograms generally indicate data, and rectangles with a pair of double borders generally indicate predefined functional elements. In method flow charts, rectangles generally indicate method steps and diamond shapes generally indicate decision elements. All of these conventions, however, are intended to be typical or illustrative, rather than limiting.

DETAILED DESCRIPTION

Systems, methods, and software products to display data from experiments with synthesized and/or spotted arrays are described herein with respect to illustrative, non-limiting, implementations. Various other alternatives, modifications and equivalents are possible. For example, while certain systems, methods, and computer software products are described using exemplary embodiments with reference to spotted arrays analyzed and displayed using Affymetrix® scanners and/or Affymetrix software, the systems, methods, and products of the present invention are not so limited. For example, they generally may be applied with respect to many other probe arrays, including many types of parallel biological assays.

Probe Arrays

For example, certain systems, methods, and computer software products are described herein using exemplary implementations for acquiring, analyzing, and/or displaying data from arrays of biological materials produced by the Affymetrix® 417™ or 427™ Arrayers available from Affymetrix, Inc. Other illustrative implementations may be referred to in relation to data from experiments with Affymetrix® GeneChip® arrays. However, these systems, methods, and products may be applied with respect to many other types of probe arrays and, more generally, with respect to numerous parallel biological assays produced in accordance with other conventional technologies and/or produced in accordance with techniques that may be developed in the future. For example, aspects of the systems, methods, and products described herein may, in some implementations, be applied to parallel assays of nucleic acids, PCR products generated from cDNA clones, proteins, antibodies, or many other biological materials. These materials may be disposed on slides (as typically used for spotted arrays), on substrates employed for GeneChip® arrays, or on beads, optical fibers, or other substrates, supports, or media (all or any of which may hereafter generally and collectively be referred to as "substrates"). Some implementations of synthesized arrays, their preparation, substrates, and the like are described in U.S. Pat. Nos. 5,744, 305 and 5,445,934, which are hereby incorporated herein by reference in their entireties for all purposes. Moreover, with respect to some implementations in which the context so indicates or allows, the probes need not be immobilized in or on a substrate, and, if immobilized, need not be disposed in regular patterns or arrays. For convenience, the term "probe array" will generally be used broadly hereafter to refer to all of these types of arrays and parallel biological assays.

For convenience, an array made by depositing or positioning pre-synthesized or pre-selected probes on a substrate, or by depositing/positioning techniques that may be developed in the future, is hereafter referred to as a "spotted array." Typically, but not necessarily, spotted arrays are commercially fabricated on microscope slide's. These arrays often consist of liquid spots containing biological material of potentially varying compositions and concentrations. For instance, a spot in the array may include a few strands of short polymers, such as oligonucleotides in a water solution, or it may include a high concentration of long strands of polymers, such as complex proteins. The Affymetrix® 417™ and 427™ Arrayers, noted above, are devices that deposit densely packed arrays of biological material on a microscope slide in accordance with these techniques. Aspects of these, and other, spot arrayers are described in U.S. Pat. Nos. 6,121,048, 6,040,193 and 6,136,269, in PCT Applications Nos. PCT/US99/00730 (International Publication Number WO99/36760) and PCT/US 01/04285, in U.S. patent applications Ser. Nos. 09/122,216, 09/501,099, and 09/862,177, and in U.S. Provisional Patent Application Ser. No. 60/288,403, all of which are hereby incorporated by reference in their entireties for all purposes. Other techniques for depositing or positioning biological probes on a substrate, i.e., creating spotted arrays, also exist. For example, U.S. Pat. No. 6,040,193 to Winkler, et al. is directed to processes for dispensing drops of biological material. The '193 patent, and U.S. Pat. No. 5,885, 837 to Winkler, also describe separating reactive regions of a substrate from each other by inert regions and spotting on the reactive regions. The '193 and '837 patents are hereby incorporated by reference in their entireties. Other techniques for producing spotted arrays are based on ejecting jets of biological material. Some implementations of the jetting technique use devices such as syringes or piezo electric pumps to propel the biological material.

Spotted arrays typically are used in conjunction with tagged biological samples such as cells, proteins, genes or EST's, other DNA sequences, or other biological elements. These samples, referred to herein as "targets," typically are processed so that they are spatially associated with certain probes in the probe array. In one non-limiting implementation, for example, one or more chemically tagged biological samples, i.e., the targets, are distributed over the probe array. Some targets hybridize with at least partially complementary probes and remain at the probe locations, while non-hybridized targets are washed away. These hybridized targets, with their "tags" or "labels," are thus spatially associated with the targets' complementary probes. The associated probe and target may sometimes be referred to as a "probe-target pair." Detection of these pairs can serve a variety of purposes, such as to determine whether a target nucleic acid has a nucleotide sequence identical to or different from a specific reference sequence. See, for example, U.S. Pat. No. 5,837,832 to Chee, et al. Other uses include gene expression monitoring and evaluation (see, e.g., U.S. Pat. No. 5,800,992 to Fodor, et al.; U.S. Pat. No. 6,040,138 to Lockhart, et al.; and International App. No. PCT/US98/15151, published as WO99/05323, to Balaban, et al.), genotyping (U.S. Pat. No. 5,856,092 to Dale, et al.), or other detection of nucleic acids. The '832, '992, '138, and '092 patents, and publication WO99/05323, are incorporated by reference herein in their entirety for all purposes.

To ensure proper interpretation of the term "probe" as used herein, it is noted that contradictory conventions exist in the relevant literature. The word "probe" is used in some contexts in the literature to refer not to the biological material that is deposited on a substrate, as described above, but to what has been referred to herein as the "target." To avoid confusion, the term "probe" is used herein to refer to compounds such as those deposited on a substrate to create spotted arrays, or oligonucleotides on synthesized arrays, as non-limiting examples.

Probe Array Experiment Systems

FIG. 1 is a simplified schematic diagram of illustrative systems for generating, sharing, and processing data derived from experiments using probe arrays (i.e., spotted arrays and/or synthesized arrays). More particularly, an illustrative arrayer system 148 and illustrative scanner systems 150A and 150B (collectively, scanner systems 150) are shown. Arrayer system 148 includes arrayer 120 that may be any type of arrayer for depositing probes to create spotted arrays such as, for example, the Affymetrix 417™ or 427™ Arrayers noted above. Further details of illustrative arrayers are provided in U.S. patent application Ser. No. 09/682,076, hereby incorporated by reference in its entirety for all purposes. In the presently illustrated example, data may be communicated among user computer 100A of system 148, user computers 100B and 100C of systems 150, and Laboratory Information Management (LIMS) server 120 over network 125. LIMS server 120 and associated software generally provides data capturing, tracking, and analysis functions from a centralized infrastructure. Aspects of a LIMS are described in U.S. Provisional Patent Application Nos. 60/220,587 and 60/273,231, both of which are hereby incorporated by reference herein for all purposes. LIMS server 120 and network 125 are optional, and the systems in other implementations may include a scanner for spotted arrays and not synthesized arrays, or vice versa. Also, rather than employing separate user computers 100A and 100B to operate and process data from an arrayer and scanner, respectively, as in the illustrated implementation, a single computer may be used for all of these purposes in other implementations. More generally, a large variety of computer and/or network architectures and designs may be employed, and it will be understood by those of ordinary skill in the relevant art that many components of typical computer network systems are not shown in FIG. 1 for sake of clarity.

User Computer 100A

As shown in FIG. 1 and noted above, arrayer 120 operates in the illustrated implementation under computer control, e.g., under the control of user computer 100A. Although computer 100A is shown in FIG. 1 for clarity as being directly coupled to arrayer 120, it may alternatively be coupled to arrayer 120 over a local-area, wide-area, or other network, including an intranet and/or the Internet.

Figure 2:
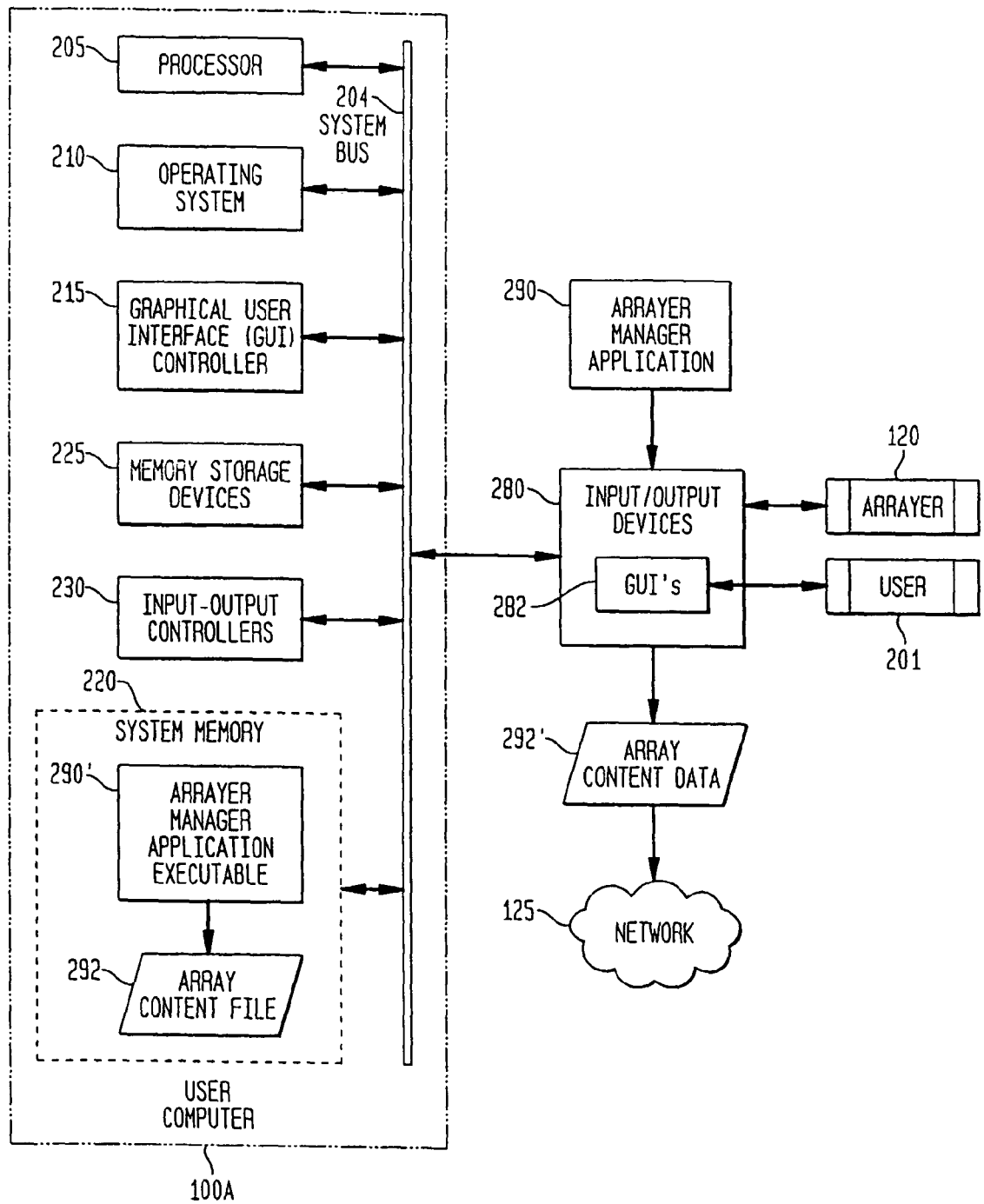
FIG. 2 is a functional block diagram of one embodiment of a user computer of the networked computers of FIG. 1 suitable for controlling the arrayer of FIG. 1 to produce spotted arrays.

FIG. 2 is a functional block diagram showing an illustrative implementation of computer 100A. Computer 100A may be a personal computer, a workstation, a server, or any other type of computing platform now available or that may be developed in the future. Typically, computer 100A includes known components such as processor (e.g., CPU) 205, operating system 210, system memory 220, memory storage devices 225, graphical user interface (GUI) controller 215, and input-output controllers 230, all of which typically communicate in accordance with known techniques such as via system bus 204. It will be understood by those skilled in the relevant art that there are many possible configurations of the components of computer 100A and that some components that may typically be included in computer 100A are not shown, such as cache memory, a data backup unit, and many other devices.

Input-output controllers 230 could include any of a variety of known devices for accepting and processing information from a user, whether a human or a machine, whether local or remote. Such devices include, for example, modem cards, network interface cards, sound cards, or other types of controllers for any of a variety of known input devices. Output controllers of input-output controllers 230 could include controllers for any of a variety of known display devices for presenting information to a user, whether a human or a machine, whether local or remote. If one of these display devices provides visual information, this information typically may be logically and/or physically organized as an array of picture elements, sometimes referred to as pixels. GUI controller 215 may comprise any of a variety of known or future software programs for providing graphical input and output interfaces between computer 100A and a user 201 (e.g., an experimenter wishing to use arrayer 120 to generate spotted arrays), and for processing inputs from user 201 (hereafter sometimes referred to as user inputs or user selections).

Arrayer Manager Application 290

Arrayer manager application 290 of the illustrated implementation is a software application that controls functions of arrayer 120 and processes data supplied by user 201. As more particularly described with respect to certain implementations in U.S. Provisional Patent Application Ser. No. 60/288, 403, incorporated by reference above, application 290, when executed in coordination with processor 205, operating system 210, and/or GUI controller 215, performs user interface functions, data processing operations, and data transfer and storage operations. For example, with respect to user interface functions, user 201 may employ one or more of GUI's 282 to specify and describe particular clones and their location in particular wells of particular well plates. Using another of GUI's 282, user 201 may specify how spots of the clones are to be arranged in arrays on one or more slides, as described in greater detail below with respect to fields 304 and 306 of array content file 292 shown in FIG. 3A. Yet another of GUI's 282 may be used to operate arrayer 120, e.g., to initiate the spotting of a number of slides without further user participation.

As will be evident to those skilled in the relevant art, application 290 may be loaded into system memory 220 and/or memory storage device 225 through an input device of devices 280. Alternatively, application 290 may be implemented as executable instructions stored in firmware. Executable code corresponding to application 290 is referred to as arrayer manager application executable 290' and is shown for convenience with respect to the illustrated implementation as stored in system memory 220. However, instructions and data including executable instructions of application 290, and data used or generated by it, may be located in or shifted among other memory devices, local or remote, as convenient for data storage, data retrieval, and/or execution.

FIG. 3A is a graphical representation of illustrative data records in one implementation of a data file generated by arrayer manager application executable 290'. The data file in this illustration, referred to as array content file 292, consists of records 301, each one of which (i.e., records 301A through 301N for any number of N records) corresponds to one of N spots, i.e., probes, that have been deposited, or are planned to be deposited, on spotted arrays 121. For example, with reference to the graphical representation of spotted arrays 121 shown in FIG. 3B, two arrays 121A and 121B (collectively, arrays 121) have been printed on microscope slide substrate 333 by arrayer 120. Array 121A includes probe 370A. It is assumed for purposes of illustration that data relating to probe 370A is stored by executable 290' in probe record 301A. In this example, each of the records in file 292 includes the following illustrative fields: probe identifier(s) 302, probe x-coordinate identifier(s) 304, probe y-coordinate identifier(s) 306, probe data 308, probe data links 310, pin identifier 312, well plate identifier 316, and user-supplied data 320.

The field in record 301A labeled probe identifier(s) 302A thus, in this example, includes certain information related to the identification of probe 370A. For instance, field 302A may include a name for cDNA deposited by a pin of arrayer 120 in array 121A to produce probe 370A. In various implementations, field 302A may also, or in addition, include a nucleotide identifier and/or a gene symbol that identifies probe 370A. Also, field 302A may include a build or release number of a database so that the data source used to develop the probe can be identified. As yet another example of information that may be included in field 302A, a probe may be identified as either an original or as a replicate. For instance, for quality control or other reasons, probe 370B of array 121A may be the same probe as probe 370A, or a number of such replicate probes may be deposited. The designation of original or replicate number assists in comparing results from probes that are based on the same sample. As one of ordinary skill in the relevant art will readily appreciate, all or some of this identifying data may be stored as a single value in field 302A (such as, for example, concatenating name, nucleotide identifier, etc.), in separate fields (e.g., 302A', 302A", etc., not shown), in linked fields, and so on as may be convenient for data storage and/or processing. The other fields described below similarly are only representative of many possible storage and data retrieval architectures.

Field 308A, labeled probe data in this example, may include probe-related data such as the chromosome location of the gene or EST represented by the probe, the band location on the chromosome, a SNP or other type of marker that can identify the location on the chromosome, and so on. Field 310A, labeled probe data links in this example, similarly may include an accession number from GenBank, a UniGene cluster number, and/or another identifier that facilitates access to data related to probe 370A that is stored in a database. This database may, but need not, be external to computer 100A and accessed via network 125 and/or the Internet or other network. Systems for providing access to such information are described, for example, in U.S. Provisional Patent Application, Ser. No. 60/288,429, hereby incorporated herein by reference in its entirety. Field 312A of this example identifies the pin on the print head(s) that is used to deposit probe 370A onto the slide. This information may be useful in comparing probes deposited with the same pin to determine, for example, if the pin is defective. Fields 314A and 316A contain information that respectively identifies the well plate and particular well from which biological fluid was taken to create probe 370A. Field 320A may contain a variety of data supplied by user 201 such as the user's name, the data of the experiment, and so on. It will be understood that there are many other types of data relating to probe 370A that may be stored, and that numerous alternative arrangements may be implemented for storing them.

Fields 304A and 306A are used to identify the location of probe 370A on the slide in x and y coordinates, respectively. It will be understood that other coordinate systems (e.g., radial system) could be used, and that the definition of the orientation and zero points of the coordinate references of the present example are illustrative only. In one implementation of the present example, field 304A could include primary and secondary row coordinates, and field 306A could include primary and secondary column coordinates, that identify the position of probe 370A. For instance, arrays 121A and 121B could be viewed as arranged in a single primary column (disposed horizontally in FIG. 3B) in which array 121A occupies the first primary row and array 121B occupies the second primary row. Such an implementation may be said to involve relative, rather than absolute, locations because locations of probes are specified in relation to each other rather than in relation to a reference point on the substrate. It may be advantageous in some implementations to specify absolute, rather than relative, locations. In one such implementation, orthogonal x and y axes could be defined in relation to the sides of the microscope slide, such as x axis 392 and y axis 394 of the illustrated example, with the 0,0 reference coordinates defined with reference to a particular point on the slide. For instance, some slides are manufactured with a frosted area, such as area 380 of this example, so that a user may more easily label or write on the slide, or for other reasons. A particular point at a corner of the frosted area could readily be defined as the reference coordinate, or any of various other methods could be used to specify a reference coordinate on, or spatially related to, a point on the substrate.

Scanner 160A: Optics and Detectors

Any of a variety of conventional techniques, or ones to be developed in the future, may be used to generate probe-target pairs in probe arrays that may be detected using a scanner. As one illustrative example that will be familiar to those of ordinary skill in the relevant art, conventional fluidics stations, hybridization chambers, and/or various manual techniques (as, for example, generally and collectively represented by hybridization process 122 in FIG. 1) may be used to apply one or more labeled targets to spotted arrays on microscope slides. In a particular implementation, for instance, sample of a first target may be labeled with a first dye (an example of what may more generally be referred to hereafter as an "emission label") that fluoresces at a particular characteristic frequency, or narrow band of frequencies, in response to an excitation source of a particular frequency. A second target may be labeled with a second dye that fluoresces at a different characteristic frequency. The excitation source for the second dye may, but need not, have a different excitation frequency than the source that excites the first dye, e.g., the excitation sources could be the same, or different, lasers. The target samples may be mixed and applied to the probes of spotted arrays on microscope slides, and conditions may be created conducive to hybridization reactions, all in accordance with known techniques. In accordance with other techniques, such as typically are applied with respect to Affymetrix® Gene-Chip® synthesized arrays, samples of one labeled target are applied to one array and samples of a second labeled target are applied to a second array having the same probes as the first array. Hybridization techniques are applied to both arrays. For example, synthesized arrays 134 of FIG. 1 may be illustratively assumed to be two GeneChip® synthesized arrays that have been subject to hybridization processes with respect to two different target samples, each labeled with different fluorescent dyes. See, e.g., U.S. Pat. No. 6,114,122, which is hereby incorporated by reference herein in its entirety.

Many scanner designs may be used to provide excitation signals to excite labels on targets or probes, and to detect the emission signals from the excited labels. In references herein to illustrative implementations, the term "excitation beam" may be used to refer to light beams generated by lasers to provide the excitation signal. However, excitation sources other than lasers may be used in alternative implementations. Thus, the term "excitation beam" is used broadly herein. The term "emission beam" also is used broadly herein. As noted, a variety of conventional scanners detect fluorescent or other emissions from labeled target molecules or other material associated with biological probes. Other conventional scanners detect transmitted, reflected, refracted, or scattered radiation from such targets. These processes are sometimes generally and collectively referred to hereafter for convenience simply as involving the detection of "emission beams." The signals detected from the emission beams are generally referred to hereafter as "emission signals" or "emissions," and these terms are intended to have a broad meaning commensurate with that intended herein for the term "emission beams."

Various detection schemes are employed depending on the type of emissions and other factors. A typical scheme employs optical and other elements to provide an excitation beam, such as from a laser, and to selectively collect the emission beams. Also generally included are various lightdetector systems employing photodiodes, charge-coupled devices, photomultiplier tubes, or similar devices to register the collected emission beams. For example, a scanning system for use with a fluorescently labeled target is described in U.S. Pat. No. 5,143,854, hereby incorporated by reference in its entirety for all purposes. Other scanners or scanning systems are described in U.S. Pat. Nos. 5,578,832, 5,631,734, 5,834,758, 5,936,324, 5,981,956, 6,025,601, 6,141,096, 6,185,030, 6,201,639, 6,218,803, and 6,252,236; in PCT Application PCT/US99/06097 (published as WO99/47964); in U.S. patent application, Ser. No. 09/681,819; and in U.S. Provisional Patent Application Ser. No. 60/286,578, each of which also is hereby incorporated herein by reference in its entirety for all purposes.

Figure 4:
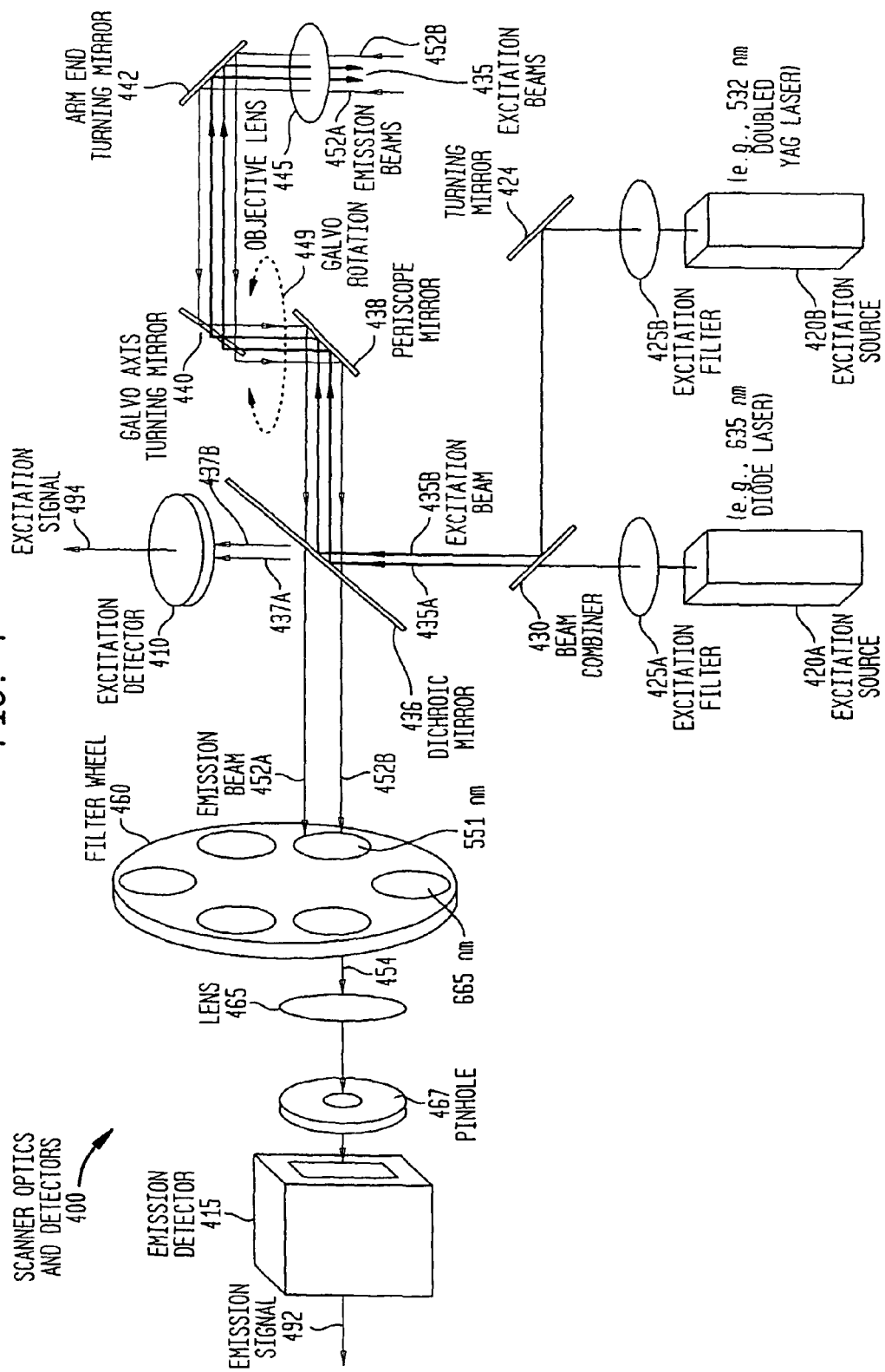
FIG. 4 is a simplified graphical representation of selected components of one embodiment of a scanner of FIG. 1 suitable for scanning arrays.

FIG. 4 is a simplified graphical representation of selected components of an illustrative type of scanner 160A suitable for scanning hybridized spotted arrays 132A and 132B disposed on slide 333 (i.e., in this example, spotted arrays 121A and 121B, respectively, after hybridization process 122). These illustrative components, which will be understood to be non-limiting and not exhaustive, are referred to collectively for convenience as scanner optics and detectors 400. Scanner optics and detectors 400 include excitation sources 420A and 420B (collectively referred to as excitation sources 420). Any number of one or more excitation sources 420 may be used in alternative embodiments. In the present example, sources 420 are lasers; in particular, source 420A is a diode laser producing red laser light having a wavelength of 635 nanometers and, source 420B is a doubled YAG laser producing green laser light having a wavelength of 532 nanometers. Further references herein to sources 420 generally will assume for illustrative purposes that they are lasers, but, as noted, other types of sources, e.g., x-ray sources, may be used in other implementations.

Sources 120A and 120B may alternate in generating their respective excitation beams 435A and 435B between successive scans, groups of successive scans, or between full scans of an array. Alternatively, both of sources 120 may be operational at the same time. For clarity, excitation beams 435A and 435B are shown as distinct from each other in FIG. 4. However, in practice, turning mirror 424 and/or other optical elements (not shown) typically are adjusted to provide that these beams follow the same path.

Scanner optics and detectors 400 also includes excitation filters 425A and 425B that optically filter beams from excitation sources 420A and 420B, respectively. The filtered excitation beams from sources 420A and 420B may be combined in accordance with any of a variety of known techniques. For example, one or more mirrors, such as turning mirror 424, may be used to direct filtered beam from source 420A through beam combiner 430. The filtered beam from source 420B is directed at an angle incident upon beam combiner 430 such that the beams combine in accordance with optical properties techniques well known to those of ordinary skill in the relevant art. Most of combined excitation beams 435 are reflected by dichroic mirror 436 and thence directed to periscope mirror 438 of the illustrative example. However, dichroic mirror 436 has characteristics selected so that portions of beams 435A and 435B, referred to respectively as partial excitation beams 437A and 437B and collectively as beams 437, pass through it so that they may be detected by excitation detector 410, thereby producing excitation signal 494.

Figure 5A:
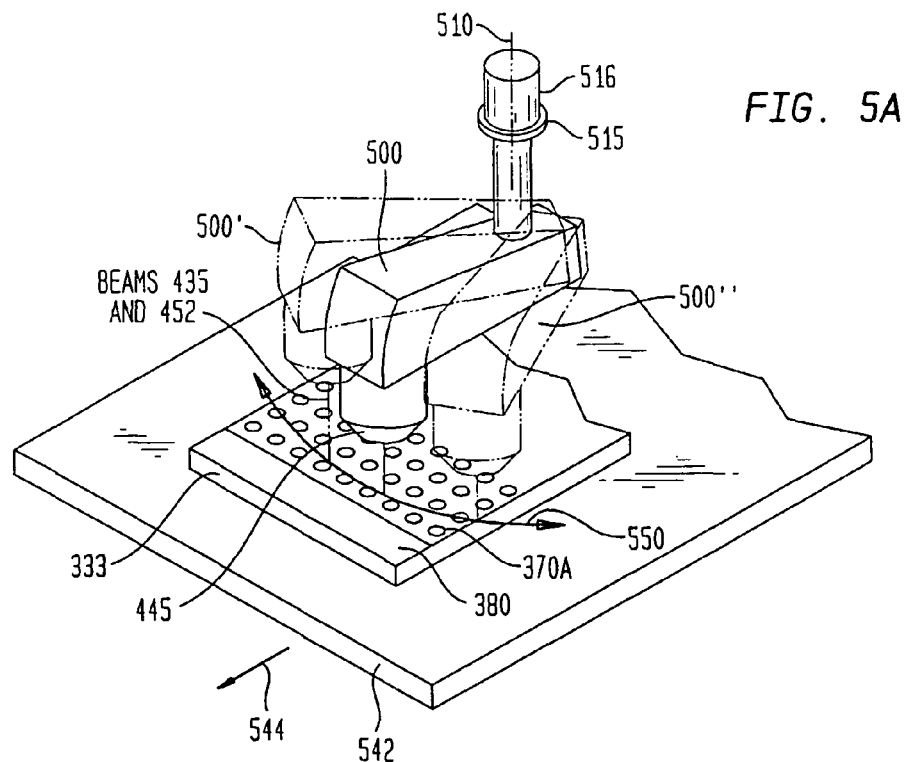
FIG. 5A is a perspective view of a simplified exemplary configuration of a scanning arm portion of the scanner of FIG. 4.
Figure 5B:
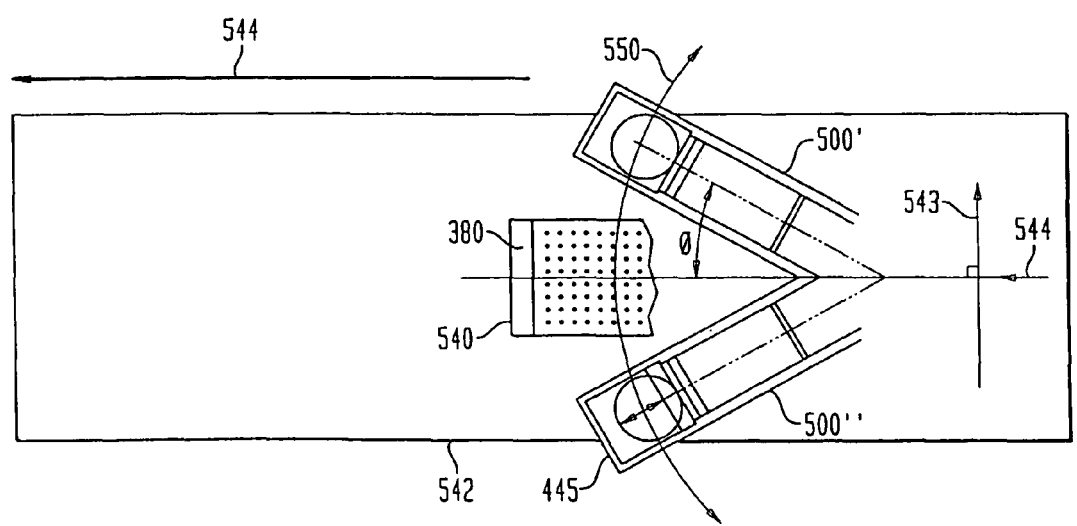
FIG. 5B is a top planar view of the scanning arm of FIG. 5A as it scans biological features on one embodiment of a spotted array being moved by a translation stage under the arm's arcuate path.

In the illustrated example, excitation beams 435 are directed via periscope mirror 438 and arm end turning mirror 442 to an objective lens 445. As shown in FIGS. 5A and 5B, lens 445 in the illustrated implementation is a small, lightweight lens located on the end of an arm that is driven by a galvanometer around an axis perpendicular to the plane represented by galvo rotation 449 shown in FIG. 4. Objective lens 445 thus, in the present example, moves in arcs over hybridized spotted arrays 132 disposed on slide 333. Flourophores in hybridized probe-target pairs of arrays 132 that have been excited by beams 435 emit emission beams 452 (beam 452A in response to excitation beam 435A, and beam 452B in response to excitation beam 435B) at characteristic wavelengths in accordance with well-known principles. Emission beams 452 in the illustrated example follows the reverse path as described with respect to excitation beams 435 until reaching dichroic mirror 436. In accordance with wellknown techniques and principles, the characteristics of mirror 436 are selected so that beams 452 (or portions of them) pass through the mirror rather than being reflected.

In the illustrated implementation, filter wheel 460 is provided to filter out spectral components of emission beams 452 that are outside of the emission band of the fluorophore, thereby providing filtered beams 454. The emission band is determined by the characteristic emission frequencies of those fluorophores that are responsive to the frequencies of excitation beams 435. In accordance with techniques well known to those of ordinary skill in the relevant arts, including that of confocal microscopy, filtered beams 454 may be focused by various optical elements such as lens 465 and also passed through illustrative pinhole 467 or other element to limit the depth of field, and thence impinges upon emission detector 415.

Emission detector 415 may be a silicon detector for providing an electrical signal representative of detected light, or it may be a photodiode, a charge-coupled device, a photomultiplier tube, or any other detection device that is now available or that may be developed in the future for providing a signal indicative of detected light. For convenience of illustration, detector 415 will hereafter be assumed to be a photomultiplier tube (PMT). Detector 415 thus generates emission signal 492 that represents numbers of photons detected from filtered emission beam 454.

FIG. 5A is a perspective view of a simplified representation of the scanning arm portion of scanner optics and detectors 400. Arm 500 moves in arcs around axis 510, which is perpendicular to the plane of galvo rotation 449. A position transducer 515 is associated with galvanometer 515 that, in the illustrated implementation, moves arm 500 in bi-directional arcs. Transducer 515, in accordance with any of a variety of known techniques, provides an electrical signal indicative of the radial position of arm 500. Certain non-limiting implementations of position transducers for galvanometer-driven scanners are described in U.S. Pat. No. 6,218,803, which is hereby incorporated by reference in its entirety for all purposes. The signal from transducer 515 is provided in the illustrated implementation to user computer 100B so that clock pulses may be provided for digital sampling of emission signal 492 when arm 500 is in certain positions along its scanning arc.

Arm 500 is shown in alternative positions 500' and 500" as it moves back and forth in scanning arcs about axis 510. Excitation beams 435 pass through objective lens 445 on the end of arm 500 and excite fluorophore labels on targets hybridized to certain of probes 370 in arrays 132 disposed on slide 333, as described above. The arcuate path of excitation beams 435 is schematically shown for illustrative purposes as path 550. Emission beams 452 pass up through objective lens 445 as noted above. Slide 333 of this example is disposed on translation stage 542 that is moved in what is referred to herein as the "y" direction 544 so that arcuate path 550 repeatedly crosses the plane of arrays 132.

FIG. 5B is a top planar view of arm 500 with objective lens 445 scanning arrays 132 as translation stage 542 is moved under path 550. As shown in FIG. 5B, arcuate path 550 of this example is such that arm 500 has a radial displacement of θ in each direction from an axis parallel to direction 544. What is referred to herein as the "x" direction, perpendicular to y-direction 544, is shown in FIG. 5B as direction 543. Further details of confocal, galvanometer-driven, arcuate, laser scanning instruments suitable for detecting fluorescent emissions are provided in PCT Application PCT/US99/06097 (published as WO99/47964) and in U.S. Pat. Nos. 6,185,030 and 6,201,639, all of which have been incorporated by reference above. It will be understood that although a galvanometer-driven, arcuate, scanner is described in this illustrative implementation, many other designs are possible, such as the voice-coil-driven scanner described in U.S. patent application, Ser. No. 09/383,986, hereby incorporated herein by reference in its entirety for all purposes.

FIG. 6A is a simplified graphical representation of illustrative probe 370A as it is scanned by scanner 160A. It is assumed for illustrative purposes that probe 370A has hybridized with a fluorescently labeled target. Although FIG. 6A shows probe 370A in idealized form, i.e. a perfect circle, it will be understood that many shapes, including irregular shapes, are possible.

In the manner described above, objective lens 445 scans over probe 370A (and other probes of arrays 132) in bi-directional arcs. An illustrative scan 620 is shown in FIG. 6A, which is not necessarily drawn to scale; e.g., the ratio of the radius of the arc of scan 620 to the radius of probe 370A is illustrative only. As also noted, probe 370A moves under objective lens 445 carried by translation stage 542 in y-direction 544. In particular, in the illustrated implementation, arm 500 scans in an arc in one direction, shown as left-to-right scan 620 in FIG. 6A. Translation stage 542 is then moved incrementally by a stepping motor (not shown) in y-direction 544 and arm 500 then scans back in the opposite direction, shown as right-to-left arcuate scan 622. Translation stage 542 is again moved in direction 544, and so on in scan-step-scan-step sequences. The distance between scans 620 and 622 thus corresponds to the distance that translation stage 542 is moved in each increment, although it will be understood that the distance shown in FIG. 6A is not necessarily to scale and is illustrative only. It will be understood that any other combination of scanning and stepping is possible in alternative implementations, and that scanning and moving of translation stage 542 may occur at the same or at overlapping times in some implementations. Translation stage 542 need not be stepped in some implementations, but may, for example, be moved continuously.

FIG. 6B is a plot having a pixel clock axis 630 showing when clock pulses 632 occur. Clock pulses 632 may be generated by a pixel clock of scanner 160A (e.g., complex programmable logic device 830, described below) or, alternatively, they may be generated by software executing in computer 100B (e.g., executable 790', described below). Axis 630 in the illustrated implementation is a spatial axis; that is, each of clock pulses 632 occurs in reference to the radial location of arm 500 during each scan, as described in greater detail below. Thus, with reference to the position of translation stage 542 indicated by scan 620, a clock pulse 632A occurs prior to arm 500 passing over probe 370A from the left as shown in FIGS. 6A and 6B. (For sake of clarity of illustration only, vertical dotted lines are provided between FIGS. 6A and 6B, and between FIGS. 6B and 6C, to illustrate the alignment of these figures.) As another example, clock pulse 632C occurs with respect to scan 620 when arm 500 has just passed over portions of probe 370A indicated by pixel areas 610A and 610B. These areas are referred to as pixel areas because a digital value is assigned to each such area in the illustrated implementation based on the strength of a processed emission signal associated with that area. In accordance with known techniques, clock pulses 632 enable the digital sampling of the processed emission signal.

As noted, clock pulses 632 are spatially rather than temporally determined in the illustrated implementation. Moreover, in some aspects of the illustrated implementation, galvanometer 516 is driven by a control signal provided by user computer 100B such that the velocity of arm 500 in x-direction 444 is constant in time during those times when arm 500 is over probe 370A (and, typically, over other of probes 370 of arrays 132 as they are scanned). That is, dx/dt is a constant (and thus the angular velocity varies) over the probe-scanning portions of each arc and, in particular, it is a constant during the times when clock pulses are generated to enable digital sampling. As is evident, dx/dt must be reduced to zero between each successive scan, but this deceleration and reversal of direction takes place after arm 500 has passed over probe 370A (or, more generally, array 132A or 132B). The design and implementation of a galvanometer control signal to provide constant dx/dt are readily accomplished by those of ordinary skill in the relevant art.

Thus, the approximate sampling rate may readily be calculated based on the desired scanning speed (dx/dt) and desired pixel resolution. To provide an illustrative example, a spot deposited by an Affymetrix® 417™ or 427™ Arrayer typically has a diameter of approximately 150 to 200 microns. Spotted arrays made using these instruments typically may be deposited over a surface having a width of about 22 millimeters on a microscope slide that is 25 millimeters wide. In order to achieve pixel resolution of about 10 microns, a sampling rate of about 160 kHz is sufficient for scanning speeds typical for scanners used with respect to these probe arrays, such as the Affymetrix® 428™ scanner. Other sampling rates, readily determined by those of ordinary skill, may be used in other applications in which, for example, different scanning speeds are used and/or different pixel resolutions are desired. The desired pixel resolution typically is a function of the size of the probe features, the possibility of variation in detected fluorescence within a probe feature, and other factors.

FIG. 6C shows digital values representative of emission signal 492 as sampled at (and/or collected for an adjoining period before) points on scans 620 and 622 represented by constant radial position lines 625A-K (collectively referred to as radial position lines 625). The voltages sampled during scan 620 are shown as dots, while the voltages sampled during scan 622 are shown as x's. The determination of when to initiate pixel clock signals may be made using position transducer 515, as described in greater detail in U.S. Provisional Patent Application Ser. No. 60/286,578, incorporated by reference above. Thus, for example, voltage 650C of FIG. 6C is representative of emission signal 492 based on sampling enabled by a pixel clock pulse at point 632C on axis 630 that is triggered when arm 500 is at radial position 625C during scan 620. After translation stage 542 has been incremented, voltage 652C is sampled during scan 622 at the same radial position, shown as radial position 625C".

User Computer 100B

Figure 7:
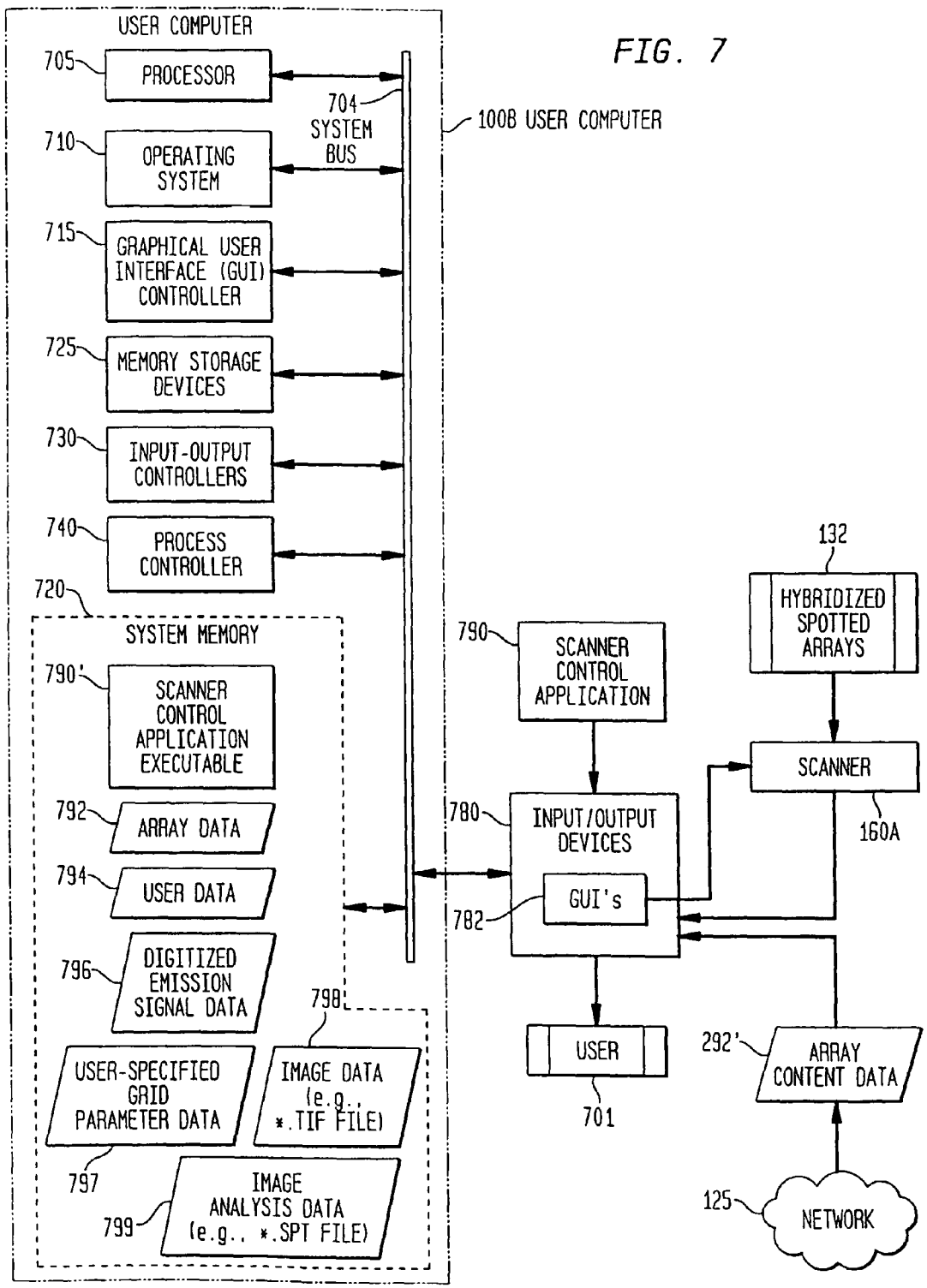
FIG. 7 is a functional block diagram of one embodiment of a scanner system of FIG. 1.

As shown in FIG. 1 and noted above, scanner 160B operates in the illustrated implementation under computer control, e.g., under the control of user computer 100B, as shown in greater detail in FIG. 7. Although computer 100B is shown in FIGS. 1 and 7 for clarity as being directly coupled to scanner 160A, it may alternatively be coupled to scanner 160A over a local-area, wide-area, or other network, including an intranet and/or the Internet. Computer 100B may be a personal computer, a workstation, a server, or any other type of computing platform now available or that may be developed in the future. Typically, computer 100B includes known components such as processor (e.g., CPU) 705, operating system 710, system memory 720, memory storage devices 725, GUI controller 715, and input-output controllers 730, all of which typically communicate in accordance with known techniques such as via system bus 704. It will be understood by those skilled in the relevant art that there are many possible configurations of the components of computer 100B and that some components that may typically be included in computer 100B are not shown, such as cache memory, a data backup unit, and many other devices.

Input-output controllers 730 could include any of a variety of known devices for accepting and processing information from a user, whether a human or a machine, whether local or remote. Such devices include, for example, modem cards, network interface cards, sound cards, or other types of controllers for any of a variety of known input devices. Output controllers of input-output controllers 730 could include controllers for any of a variety of known display devices for presenting information to a user, whether a human or a machine, whether local or remote. If one of these display devices provides visual information, this information typically may be logically and/or physically organized as an array of picture elements, sometimes referred to as pixels. Graphical user interface (GUI) controller 715 may comprise any of a variety of known or future software programs for providing graphical input and output interfaces between computer 100B and a user 701 (e.g., an experimenter wishing to use scanner 160A to acquire and analyze information from spotted arrays), and for processing inputs from user 701 (hereafter sometimes referred to as user inputs or user selections). To avoid confusion, references hereafter to a "GUI" generally are directed to one or more graphical user interfaces displayed on a display device of devices 780 to user 701, such as GUI 782A of FIGS. 8 and 9, described below. To be distinguished are references to a "GUI controller," such as GUI controller 715, that operates to display the GUI's to user 701 and to process input information provided by user 701 through the GUI's. As is well known in the relevant art, a user may provide input information using a GUI by selecting, pointing, typing, speaking, and/or otherwise operating, or providing information into, one or more input devices of devices 780 in a known manner.

Computer 100B may optionally include process controller 740 that may, for example, be any of a variety of PC-based digital signal processing (DSP) controller boards, such as the M44 DSP Board made by Innovative Integration of Simi Valley, Calif. More generally, controller 740 may be implemented in software, hardware or firmware, or any combination thereof.

Scanner Control and Analysis Application 790

Scanner control application 790 of the illustrated implementation is a software application that controls functions of scanner 160A. In addition, when executed in coordination with processor 705, operating system 710, GUI controller 715, and/or process controller 740, application 790 performs user interface functions, data and image processing operations, and data transfer and storage operations related to data provided by or to scanner 160A and/or user 701, as described in greater detail below. Affymetrix® Jaguar™ software, available from Affymetrix, Inc., is a commercial product that, in some implementations, includes various aspects of application 790.

Figure 8:
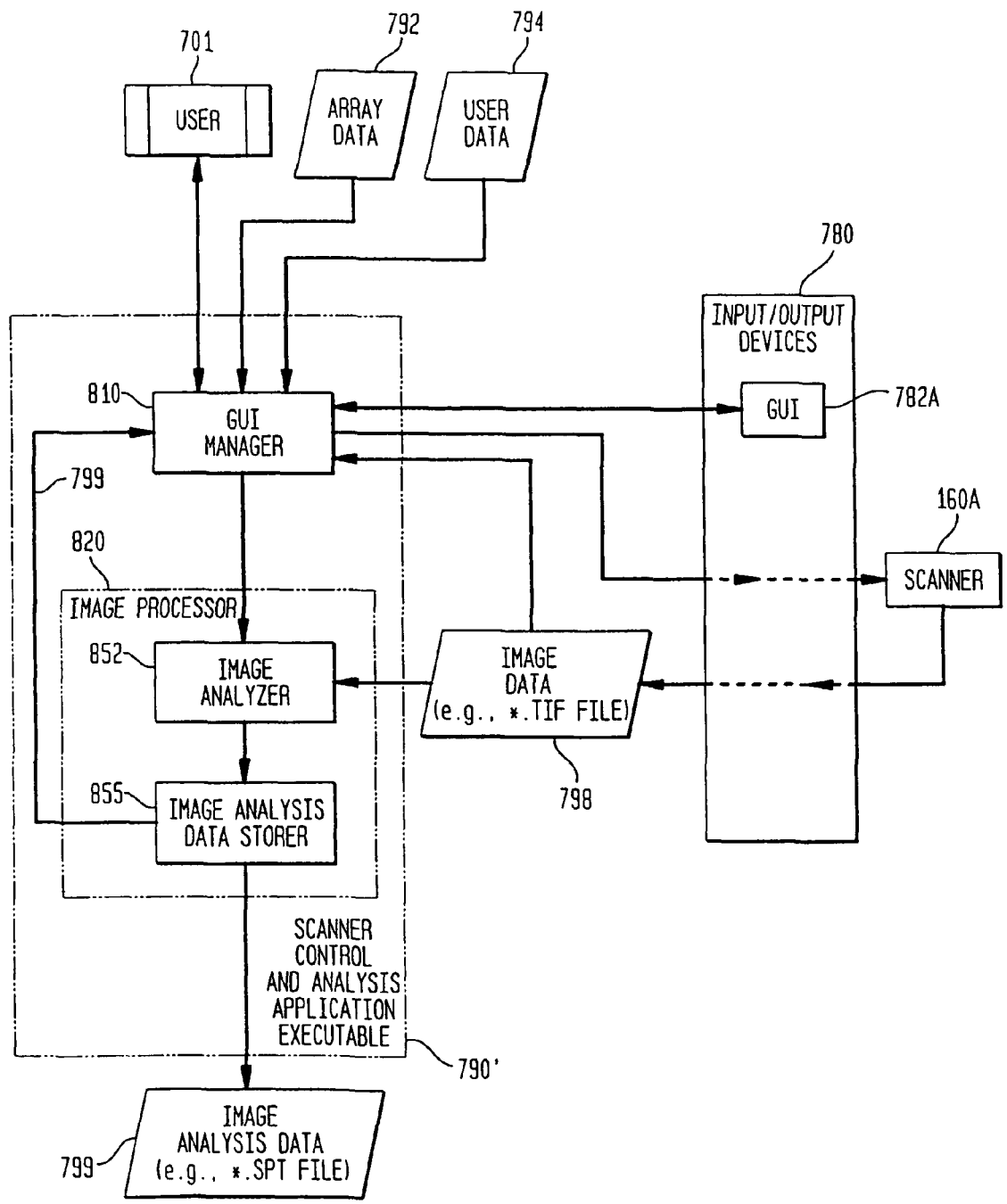
FIG. 8 is functional block diagram of one embodiment of a scanner control and analysis application (i.e., computer program product).

As more particularly shown in FIG. 8, scanner control application 790 in the illustrated implementation includes a GUI manager 810 that, in accordance with known techniques, receives and processes user selections of windows for display and user selections of features within one or more of the displayed windows. GUI manager 810 also builds and displays, in accordance with known techniques, the windows, features, and selections according to templates and other stored data as well as user data 794, array data 792, image data 798, and image analysis data 799. Also included in application 790 is image processor 820 that receives image data 798 from scanner 160A. In particular, in the illustrative implementation image analyzer 852 of processor 820 receives data 798 and analyzes it to provide image analysis data 799. Data 799 is stored by storer 855 in system memory 720 and also provided to GUI manager 810 for inclusion in GUI 782A. Similarly, image data 798 may be provided to GUI manager 810 for inclusion in GUI 782A.

Figure 9:
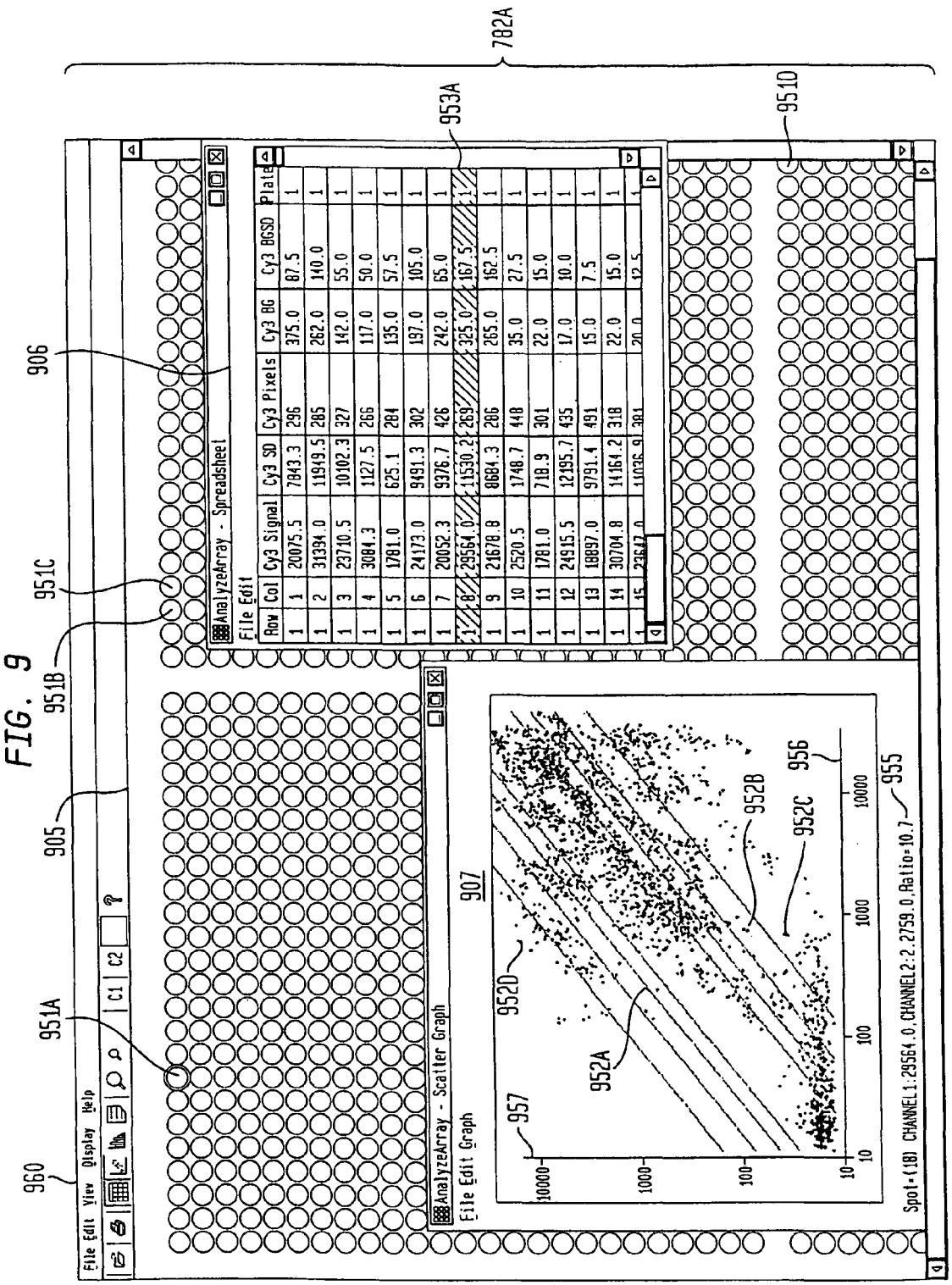
FIG. 9 is an illustrative implementation of a graphical user interface employed in cooperation with the application of FIG. 8.

For convenience of further description, it is illustratively assumed that user 701 indicates that three openable windows are to be displayed, as represented by illustrative GUI 782A of FIG. 8 and shown in greater detail in FIG. 9. It will be understood that GUI 782A of FIG. 9 is illustrative only, and that numerous variations, alternative, and/or rearrangements of the information and features described herein with respect to GUI 782A may be provided in other implementations.

It will be illustratively assumed that user 701 selects three openable windows to be displayed in GUI 782A. This selection may be accomplished in accordance with a variety of known techniques, such as by selecting the windows from a pull down menu, e.g., from "View" menu 960 of FIG. 9. As shown in FIG. 9, GUI 782A of this example thus includes first window 905 that includes a plurality of image features, referred to for convenience as spots 951, such as spots 951A-D. Spots 951 of this implementation may be considered to be pseudo-images of probes in one or more spotted arrays. Thus, for example, a visual characteristic of image feature 951A represents a hybridization reaction associated with a probe of a spotted array arranged in the upper left quadrant of first window 905. Spots 951B and 951C are associated with another spotted array, the pseudo-image of which is arranged in the upper right quadrant. Similarly, spot 951D is associated with a third spotted array, the pseudo-image of which is arranged in the lower right quadrant of first window 905. In this example, the visual characteristic may be the gray-scale intensity of spots 951. Many of spots 951 appear of equal intensity in this example, but it will be understood that this is a simplification for convenience of illustration only. In general, the intensity or other visual or other characteristic of spots 951 may vary to represent a degree, efficiency, or intensity of hybridization of a probe-target pair.

It is also illustratively assumed with respect to GUI 782A of FIG. 9 that user 701 has selected to display, i.e., open, second openable window 907 that, in this illustrative implementation, is a scatter plot or graph. Window 907 includes a plurality of data features 952, such as represented in this example by dots 952 including dots 952A-D. The placement of each of dots 952 in relation to horizontal axis 956 and vertical axis 957 of the scatter plot indicates, in this example, the intensity of hybridization of a probe in relation to emissions from a first dye attached, for example, to a first target and emissions from a second dye attached to a second target. For instance, the placement of dot 952A in relation to axis 956 indicates the intensity of an emission signal due to the probe associated with dot 952A hybridizing to a first target labeled with the first dye, and the placement of dot 952A in relation to axis 957 indicates the intensity of an emission signal due to the same probe hybridizing to a second target labeled with the second dye. In this implementation, the intensities of the emission signals, and thus the plot of window 907, are provided in log scale. However, other scales, such as linear scale, may be employed in other implementations.

In the illustrative implementation, second window 907 is displayed by overlaying it on top of first window 905. However, in alternative implementations, the windows may be displayed without overlapping or overlaying, in accordance with known techniques. Also in accordance with known techniques, any of the windows may be resized, moved, or rearranged by user 701.

It is further assumed that user 701 has selected to display third window 906 that, in this implementation, is a spreadsheet. The spreadsheet includes a plurality of descriptive features, i.e., rows in this example. Thus, for instance, row 953A is shown that provides information about a probe in the scanned probe array. The descriptive elements in this row, each arranged in a separate column, include, for example, a "Row" element having a value "1" and a "Col" element having a value "8."

It is assumed for illustrative purposes that user 701 selects row 953A. GUI manager 810 causes row 953A to be highlighted in accordance with known techniques. GUI manager 810 has populated row 953A (and the other displayed rows of the spreadsheet) with information available to manager 810 from array data 792, user data 794, image data 798 and/or image analysis data 799. For example, in the illustrated example, the values "1" in the "Row" column and "8" in the "Col" column indicate that the probe associated with row 953A is located in the first row and eighth column of the probe array. Other of array data 792, e.g., primary rows and columns as described above, may be provided in alternative examples to indicate which of the arrays shown in window 905 constitute the array in which the probe corresponding to row 953A is located. As additional examples, the value of the descriptive element of row 953A arranged under the column labeled "Cy3 Signal" indicates an intensity of the emission signal from the dye Cy3 detected by scanner 160A by scanning the probe associated with row 953A.

In accordance with some implementations of the present invention, GUI manager 810 automatically highlights the features of window 905 and window 907 corresponding to the user-selected and highlighted feature of window 906. Thus, as shown in GUI 782A of FIG. 9, GUI manager 810 causes spot 951A of window 905 to be highlighted (i.e., in this example a white circle highlights the spot's boundaries) and causes dot 952A of window 907 to be highlighted (i.e., a circle is drawn around it in this example). In addition, in this implementation textual element 955 is provided at the bottom of window 907 that shows intensity information related to the highlighted dot 952A. The preceding illustrative description could also have assumed that user 701 selected spot 951A, thus causing GUI manager 810 to highlight row 953A and dot 952A, or that user 701 selected dot 952A, causing GUI manager 810 to highlight row 953A and spot 951A. In any of these cases, dot 952A, textual element 955, spot 951A, and row 953A all provide user 701 with easily accessible and correlated information regarding a common probe. Advantageously, this information may be displayed to user 701 in simultaneously displayed windows on GUI 782A. In other examples, user 701 may have selected any two of the three illustrative windows described above.

Additional embodiments are described in the copending PCT Application PCT/US01/26297 entitled "System, Method and Computer Software Product for Controlling Biological Microarray Scanner" filed on 22 Aug. 2001, which is incorporated by reference as if fully provided herein.

Having described various embodiments and implementations of the present invention, it should be apparent to those skilled in the relevant art that the foregoing is illustrative only and not limiting, having been presented by way of example only. Many other schemes for distributing functions among the various functional elements of the illustrated embodiment are possible in accordance with the present invention. The functions of any element may be carried out in various ways in alternative embodiments. Also, the functions of several elements may, in alternative embodiments, be carried out by fewer, or a single, element.

For example, arrayer manager application 290 is described as executing on computer 100A that controls arrayer 120, and scanner control application 390 is described as executing on computer 100B that control scanner 160A. However, aspects of the invention need not be divided into these distinct functional elements. Rather, for example, applications 290 and 390 could be executed on a same computer that may, for example, control both arrayer 120 and scanner 160A. Moreover, applications 290 and 390 may be part of a same computer program product irrespective of whether they are executed on a same, or different, computers.

In addition, it will be understood by those skilled in the relevant art that control and data flows between and among functional elements of the invention and various data structures may vary in many ways from the control and data flows described above. More particularly, intermediary functional elements (not shown) may direct control or data flows, and the functions of various elements may be combined, divided, or otherwise rearranged to allow parallel processing or for other reasons. Also, intermediate data structures or files may be used, various described data structures or files may be combined, the sequencing of functions or portions of functions generally may be altered, and so on. Numerous other embodiments, and modifications thereof, are contemplated as falling within the scope of the present invention as defined by appended claims and equivalents thereto.

Copyright Statement

A portion of the disclosure of this patent document contains material that is subject to copyright protection. The copyright owner has no objection to the facsimile reproduction by anyone of the patent document or the patent disclosure as it appears in any Patent Office patent file or records, but otherwise reserves all copyright rights whatsoever.

What is claimed is:

1. A method comprising the steps of:
    (a) providing a laser source, a detector and scanner optics, said laser source being constructed and arranged to produce excitation radiation being delivered to an array including hybridized probe-target pairs, said detector being constructed to detect emitted radiation excited in a fluorophore in response to the excitation radiation, and said scanner being constructed to scan the probe array to generate image data based on sampled emission radiation received from said detector over a pixel array corresponding to the scanned probe array;
    (b) providing in a graphical user interface (GUI) at least the following windows:
        (i) a first window having a plurality of image features based on the image data, each having one or more characteristics representing one or more hybridization reactions associated with a probe of a probe array,
        (ii) a second window having a plurality of data features, each relating to one or more quantifications of one or more hybridization reactions associated with a probe of the probe array, and
        (iii) a third window having a plurality of descriptive features, each feature including at least two descriptive elements selected from the group consisting of: absolute image intensity value, probe data links, pin identifier, well plate identifier, chromosome location of a gene represented by the probe, chromosome location of an expressed sequence tag represented by the probe, band location on the chromosome, a single-nucleotide polymorphism (SNP) identifying the location on the chromosome, a non-SNP marker identifying the location on the chromosome, data related to the production of hybridization intensity data displayed in the first window, and information about the targets that hybridized with the probes.

2. The method of claim 1, further comprising the steps of:
    (c) receiving a user selection of a feature from any of the windows; and
    (d) causing a corresponding feature in at least one other window to be highlighted.

3. The method of claim 1, further comprising:
    a fourth openable window having a plurality of second image features, each having one or more characteristics representing one or more hybridization reactions associated with a probe of the array.

4. The method of claim 1, wherein the scanner provides light of two wavelengths and wherein the first image features are generated based on emissions of a first wavelength and the second image features are generated based on emissions of a second wavelength different from the first wavelength.

5. The method of claim 1, wherein the one or more characteristics of the plurality of first image features include a chromatic value representing degree, efficiency, or intensity of hybridization.

6. The method of claim 1, wherein the one or more characteristics of the plurality of first image features include an intensity value representing degree, efficiency, or intensity of hybridization.

7. The method of claim 1, wherein:
    the plurality of first image features comprises a pseudo-image of the array.

8. The method of claim 1, wherein the plurality of data features each represent a quantification of degree, efficiency, or intensity of hybridization of a probe based on the probe hybridizing with none, one or a plurality of targets.

9. The method of claim 1, wherein the plurality of descriptive features comprises rows of a spreadsheet wherein each row includes one or more descriptive elements associated with a probe.

10. The method of claim 1, wherein the descriptive elements comprise probe data links comprising links to remotely stored user-supplied data related to the probe, links to locally stored user-supplied data related to the probe, links to remotely stored biological information related to the probe, and links to locally stored biological information related to the probe.

11. The method of claim 1, wherein:
    the plurality of data features comprises a three dimensional scatter plot of emission intensity values, where each axis shows the emission intensity values of a different fluorescent dye.

12. The method of claim 1, wherein the laser source can generate the excitation radiation between successive scans, groups of successive scans, or between full scans of the scanned probe array.

13. The method of claim 1, wherein the third window comprises at least the descriptive feature of data linked to an internet-based database which contains information about the probes and/or the targets that hybridize with the probes.

14. The method of claim 13, wherein the descriptive feature in the third window is a gene sequence accession number which links the data to an internet-based genetic sequence databank.

15. The method according to claim 14, wherein the accession number corresponds to accession numbers found in GenBank or UniGene.

16. The method of claim 1, wherein each feature of the third window includes at least three descriptive elements.

17. A scanning system, comprising:
    (a) a scanner comprising a laser source, a detector and scanner optics, said laser source being constructed and arranged to produce excitation radiation being delivered to an array comprising hybridized probe-target pairs, said detector being constructed to detect emitted radiation excited in a fluorophore in response to said excitation radiation, and said scanner being constructed to scan the array to generate image data based on sampled emission radiation received from said detector over a pixel array corresponding to the scanned array;
    (b) an image processor constructed and arranged to receive image data from the scanner and to process the image data; and
    (c) a graphical user interface (GUI) manager constructed and arranged to provide at least the following windows:
        (i) a first window having a plurality of image features based on the processed image data, each having one or more characteristics representing one or more hybridization reactions associated with a probe of the probe array, (ii) a second window having a plurality of data features, each relating to one or more quantifications of one or more hybridization reactions associated with a probe of the probe array, and (iii) a third window having a plurality of descriptive features, each feature including at least two descriptive elements selected from the group consisting of: absolute image intensity value, probe data links, pin identifier, well plate identifier, chromosome location of a gene represented by the probe, chromosome location of an expressed sequence tag represented by the probe, band location on the chromosome, a single-nucleotide polymorphism (SNP) identifying the location on the chromosome, a non-SNP marker identifying the location on the chromosome, data related to the production of hybridization intensity data displayed in the first window, and information about the targets that hybridized with the probes.

18. The scanning system of claim 17, wherein the first, second, and third openable windows are all open in the interface at a same time.

19. The scanning system of claim 17, further comprising: a fourth openable window having a plurality of second image features, each having one or more characteristics representing one or more hybridization reactions associated with a probe of the array.

20. The scanning system of claim 19, wherein the scanner provides light of two wavelengths and wherein the first image features are generated based on emissions of a first wavelength and the second image features are generated based on emissions of a second wavelength different from the first wavelength.

21. The scanning system of claim 17, wherein the one or more characteristics of the plurality of first image features include a chromatic value representing degree, efficiency, or intensity of hybridization.

22. The scanning system of claim 17, wherein: the plurality of first image features comprises a pseudo-image of the array.

23. The scanning system of claim 17, wherein the plurality of data features each represent a quantification of degree, efficiency, or intensity of hybridization of a probe based on the probe hybridizing with none, one or a plurality of targets.

24. The scanning system of claim 17, wherein the plurality of descriptive features comprises rows of a spreadsheet wherein each row includes one or more descriptive elements associated with a probe.

25. The scanning system of claim 17, wherein the descriptive elements comprise probe data links comprising links to remotely stored user-supplied data related to the probe, links to locally stored user-supplied data related to the probe, links to remotely stored biological information related to the probe, and links to locally stored biological information related to the probe.

26. The scanning system of claim 17, wherein the GUI manager enables a user to select a first image feature associated with a first probe, a data feature or a descriptive feature associated with the first probe, or both, for highlighting.

27. The scanning system of claim 17, wherein the array is a spotted array.

28. The scanning system of claim 17, wherein the array is a synthesized array.

29. The scanning system of claim 17, wherein the third window comprises at least the descriptive feature of data linked to an internet-based database which contains information about the probes and/or the targets that hybridize with the probes.

30. The system of claim 17, wherein each feature of the third window includes at least three descriptive elements.

31. A scanning system, comprising:
a scanner constructed and arranged to receive probe array data and to scan a probe array to generate image data;
a computer; and
a computer program product that, when executed on the computer, performs a method comprising the steps of:
(a) receiving image data from said scanner and processing the image data, and
(b) providing in a graphical user interface (GUI) at least the following windows:
(i) a first window having a plurality of image features based on the processed image data, each having one or more characteristics representing one or more hybridization reactions associated with a probe of a probe array,
(ii) a second window having a plurality of data features, each relating to one or more quantifications of one or more hybridization reactions associated with a probe of the probe array, and
(iii) a third window having a plurality of descriptive features, each including one or more descriptive elements selected from the group consisting of: absolute image intensity value, probe data links, pin identifier, well plate identifier, chromosome location of a gene represented by the probe, chromosome location of an expressed sequence tag represented by the probe, band location on the chromosome, a single-nucleotide polymorphism (SNP) identifying the location on the chromosome, a non-SNP marker identifying the location on the chromosome, data related to the production of hybridization intensity data displayed in the first window, and information about the targets that hybridized with the probes.

32. The scanning system of claim 31, wherein:
the method performed by the computer program product further comprises the steps of
(c) receiving a user selection of a feature from any of the windows, and
(d) causing a corresponding feature in at least one other window to be highlighted.

33. The scanning system of claim 31, wherein the GUI enables a user to select a first image feature associated with a first probe, a data feature or a descriptive feature associated with the first probe, or both, for highlighting.

34. The scanning system of claim 31, wherein the descriptive elements comprise probe data links comprising links to remotely stored user-supplied data related to the probe, links to locally stored user-supplied data related to the probe, links to remotely stored biological information related to the probe, and links to locally stored biological information related to the probe.

35. The scanning system of claim 31, further comprising: a fourth openable window having a plurality of second image features, each having one or more characteristics representing one or more hybridization reactions associated with a probe of the same probe array.

36. The scanning system of claim 31, wherein the scanner provides light of two wavelengths and wherein the first image features are generated based on emissions of a first wavelength and the second image features are generated based on emissions of a second wavelength different from the first wavelength.

37. The scanning system of claim 31, wherein the scanner provides an x-ray source constructed and arranged to produce excitation radiation.

38. The scanning system of claim 31, wherein the third window comprises at least the descriptive feature of data linked to an internet-based database which contains information about the probes and/or the targets that hybridize with the probes.

* * * * *